US008968726B2

(12) United States Patent  
Naidu et al.

(10) Patent No.: US 8,968,726 B2  
(45) Date of Patent: *Mar. 3, 2015

(54) LACTOFERRIN AND ANGIOGENIN COMPOSITIONS AND USES THEREOF

(75) Inventors: A. Satyanarayan Naidu, Diamond Bar, CA (US); A. G. Tezus Naidu, Diamond Bar, CA (US); A. G. Sreus Naidu, Diamond Bar, CA (US)

(73) Assignee: Naidu LP, Pomona, CA (US)

( * ) Notice: Subject to any disclaimer, the term of this patent is extended or adjusted under 35 U.S.C. 154(b) by 674 days.

This patent is subject to a terminal disclaimer.

(21) Appl. No.: 13/204,587

(22) Filed: Aug. 5, 2011

(65) Prior Publication Data

US 2011/0286986 A1 Nov. 24, 2011

Related U.S. Application Data

(63) Continuation of application No. 11/482,653, filed on Jul. 7, 2006.

(60) Provisional application No. 60/795,871, filed on Apr. 28, 2006.

(51) Int. Cl.

| | |
|---|---|
| A61K 38/40 | (2006.01) |
| C07K 14/79 | (2006.01) |
| C07K 14/515 | (2006.01) |
| A61K 31/12 | (2006.01) |
| A61K 38/18 | (2006.01) |
| A61K 38/47 | (2006.01) |
| A61K 36/889 | (2006.01) |
| A61K 36/90 | (2006.01) |
| A61K 36/185 | (2006.01) |
| A61K 45/06 | (2006.01) |
| A61K 31/525 | (2006.01) |
| A61K 33/06 | (2006.01) |

(52) U.S. Cl.
CPC ............. *A61K 31/12* (2013.01); *A61K 38/40* (2013.01); *A61K 38/1891* (2013.01); *A61K 38/47* (2013.01); *A61K 36/889* (2013.01); *A61K 36/90* (2013.01); *A61K 36/185* (2013.01); *C12Y 302/01017* (2013.01); *A61K 45/06* (2013.01); *A61K 31/525* (2013.01); *A61K 33/06* (2013.01)
USPC ... 424/94.1; 424/93.4; 424/93.44; 424/93.45; 514/2.5

(58) Field of Classification Search
CPC ............ A61K 2300/00; A61K 36/185; A61K 36/889; A61K 36/90; A61K 38/1891; A61K 38/40; A61K 38/47; A61K 31/12; A61K 31/525; A61K 33/06; A61K 45/06; C12Y 302/01017
USPC ............ 424/94.1, 93.4, 93.44, 93.45; 514/2.5
See application file for complete search history.

(56) References Cited

U.S. PATENT DOCUMENTS

| | | | |
|---|---|---|---|
| 5,698,185 | A | 12/1997 | Itagaki et al. |
| 5,846,569 | A | 12/1998 | Anderson et al. |
| 6,066,469 | A | 5/2000 | Kruzel et al. |
| 6,172,040 | B1 | 1/2001 | Naidu |
| 6,267,985 | B1 | 7/2001 | Chen et al. |
| 6,294,579 | B1 | 9/2001 | Carnazzo |
| 6,492,429 | B1 | 12/2002 | Graus et al. |
| 6,572,868 | B1 | 6/2003 | Cope |
| 6,645,472 | B1 | 11/2003 | Anderson |
| 7,601,689 | B2 | 10/2009 | Naidu |
| 7,956,031 | B2 | 6/2011 | Naidu et al. |
| 8,003,603 | B2 | 8/2011 | Naidu |
| 8,021,659 | B2 | 9/2011 | Naidu et al. |
| 8,703,699 | B2 | 4/2014 | Cornish et al. |
| 2002/0044913 | A1 | 4/2002 | Hamilton |
| 2003/0170290 | A1 | 9/2003 | Shug et al. |
| 2004/0043922 | A1 | 3/2004 | Naidu |
| 2004/0052860 | A1 | 3/2004 | Reid et al. |
| 2004/0071825 | A1 | 4/2004 | Lockwood |
| 2004/0214750 | A1 | 10/2004 | Georgiades |
| 2005/0106194 | A1 | 5/2005 | Schiltz |
| 2005/0175597 | A1 | 8/2005 | Rawlin et al. |
| 2005/0176123 | A1 | 8/2005 | Katunuma |
| 2005/0186319 | A1 | 8/2005 | Williams et al. |
| 2005/0197495 | A1 | 9/2005 | Naidu |
| 2006/0240116 | A1 | 10/2006 | Jolley |
| 2008/0254018 | A1 | 10/2008 | Naidu |
| 2009/0148433 | A1 | 6/2009 | Naidu et al. |
| 2011/0200575 | A1 | 8/2011 | Naidu et al. |
| 2011/0286989 | A1 | 11/2011 | Naidu |

FOREIGN PATENT DOCUMENTS

| | | |
|---|---|---|
| JP | 10-007585 | 7/1990 |
| JP | 02191205 | 7/1990 |
| WO | WO 01/15715 | 3/2001 |

(Continued)

OTHER PUBLICATIONS

Arnold, et al. 1991. Engineered Metal-Binding proteins: Purification to Protein Folding. *Science*, vol. 252, pp. 1796-1797.

Baker, et al. 2005. Molecular Structure, Binding Properties and Dynamics of Lactoferrin. *Cell. Mol. Life Sci.*, vol. 62, pp. 2531-2539, 2005.

(Continued)

*Primary Examiner* — Taeyoon Kim

(74) *Attorney, Agent, or Firm* — Knobbe, Martens, Olson & Bear LLP

(57) ABSTRACT

Compositions are described which contain lactoferrin and angiogenin. The described compositions are useful in treatment of a variety of conditions, particularly in promoting bone health and relief of menopausal symptoms.

19 Claims, No Drawings

(56) References Cited

FOREIGN PATENT DOCUMENTS

| WO | WO 2004/093995 | 11/2004 |
|----|----------------|---------|
| WO | WO 2005/063184 | 7/2005  |
| WO | WO 2005/079764 | 9/2005  |
| WO | WO 2006/009825 | 1/2006  |

OTHER PUBLICATIONS

Specifications and Analysis of Bovine Colostrum, 2008. http://www.scientificneutraceuticals.com/assay.htm. p. 1-3.

Colostrum Prime Life™ 2008. http://www.jarrow.com/product/2007/Colostrum_Prime_Life. p. 1-2.

LACTOFERRIN AND ANGIOGENIN COMPOSITIONS AND USES THEREOF

RELATED APPLICATIONS

This application is a continuation of U.S. application Ser. No. 11/482,653 filed Jul. 7, 2006 which claims priority to U.S. Provisional Application No. 60/795,871, filed Apr. 28, 2006. Both applications are incorporated herein by reference.

BACKGROUND OF THE INVENTION

1. Field of the Invention

The present invention relates to methods of enhancing the bio-availability of coenzyme Q10, and supporting the cardiovascular system, and a composition including coenzyme Q10, lactoferrin and/or angiogenin for use in the described methods, for multi-functional health applications.

2. Description of the Related Art

Coenzyme Q10 (CoQ-10) is a fundamental molecule for production of cellular energy in most living organisms. It is a fat-soluble quinone (chemical nomenclature: 2,3-dimethoxy-5-methyl-6-decaprenyl-1,4-benzoquinone, CAS registry no. 303-98-0), structurally similar to vitamin K and known by the names ubiquinone, ubidecarenone, neuquinone, and vitamin-Q.

Although found in all human cells, CoQ-10 occurs at relatively elevated concentrations in cells with high energy requirements such as heart, liver, muscle, and pancreas. The total body content of CoQ-10 has been estimated at 0.5-1.5 g. Normal blood levels range from 0.7-1.0 µg/mL. Human cells synthesize CoQ-10 from the amino acid tyrosine, in an eight-step aromatic pathway, requiring adequate levels of vitamins such as folic acid, niacin, riboflavin, and pyridoxine. A nutritional deficiency in any of these precursors would lead to CoQ-10 deficiency. [Folkers K. Relevance of the biosynthesis of coenzyme Q10 and the four bases of DNA as a rationale for the molecular causes of cancer and a therapy. Biochem Biophys Res Commun 224:358-61, 1996].

CoQ-10 is located in the inner mitochondrial membrane. It is a cofactor for at least three mitochondrial enzymes (complexes I, II and III) that plays a vital role in oxidative phosphorylation. It functions as the only non-protein component of the electron transport chain (ETC). This unique characteristic enables CoQ-10 to move and transfer electrons between flavoproteins and cytochromes. Each pair of electrons processed by the ETC must first interact with CoQ10, which is considered the central rate-limiting factor for the mitochondrial respiratory chain. Therefore, CoQ10 plays an essential role in adenosine triphosphate (ATP) or biological energy production. [Levin B. Coenzyme Q: clinical monograph. Quart Rev Nat Med 3:235-249, 1994; Crane F L, Sun I L, Sun E E. The essential functions of coenzyme Q. Clin Investig 71:S55-59, 1993].

CoQ-10 is located in membranes that are in close proximity to the unsaturated lipid chains, to act as a primary scavenger of free radicals. The concentration of CoQ-10 in many such membranes is high, about 3 to 30 times more than the tocopherol content. Since much of the CoQ-10 in cell membranes is in the quinol form, it works as a potent antioxidant to scavenge free radicals, as well as inhibit lipid and protein peroxidation. CoQ-10 constantly undergoes oxidation-reduction recycling. The reduced form readily donates electrons to neutralize oxidants and displays strongest antioxidant activity. CoQ-10 is the only known naturally occurring lipid-soluble antioxidant that regenerates to its active form in the body. [Quinn P J, et al. Expansion of the antioxidant function of vitamin E by coenzyme Q. Biofactors 9: 149-154, 1999]

The membrane stabilizing property of CoQ-10 has been postulated to involve the phospholipid-protein interaction that increases prostaglandin metabolism. CoQ-10 stabilizes myocardial calcium-dependent ion channels and prevents the depletion of metabolites essential for ATP synthesis. CoQ-10 also decreases blood viscosity, and improves blood flow to cardiac muscle in patients with ischemic heart disease. [Rauchova H, et al. Function of coenzyme Q in the cell: Some biochemical and physiological properties. Physiol Res 44:209-216, 1995; Kato T, et al. Reduction in blood viscosity by treatment with coenzyme Q10 in patients with ischemic heart disease. Int J Clin Pharmacol Ther Toxicol 28:123-126, 1990].

A vital role in the production of cellular energy combined with its potent antioxidant activity makes CoQ-10 an essential health supplement. Furthermore, its multifunctional properties including vitamin-like adjuvant activity, protection against age-related degeneration, support of homeostasis, prophylactic and therapeutic effects against several diseases, makes CoQ-10 an important nutraceutical agent.

The benefits of CoQ-10 supplementation are compelling in the protective and therapeutic management of cardiovascular health. Several controlled studies have reported the clinical efficacy of CoQ-10 as a supplemental therapeutic in the treatment of congestive heart failure (CHF). Myocardial tissue levels of CoQ-10 in CHF patients is about 33% lower than control subjects. Accordingly, the severity of symptoms associated with CHF and the presence of dilated cardiomyopathy strongly correlate with the degree of CoQ-10 deficiency. The proposed mechanism of CoQ-10 activity to alleviate symptoms of CHF is by a positive inotropic action. Such activity increases the contractile force of the heart and thereby improves cardiac output. Several conventional CHF therapeutics also possess this positive inotropic property, however, an adequate supply of cellular energy is necessary for optimal contractility of the heart. Failed hearts are ATP deficient; therefore, the reason behind CoQ-10 supplementation during CHF therapy is to improve bioenergetics of the cardiac tissue. Furthermore, any improved tolerance to aerobic exercise is attributed to the ability of CoQ-10 to maintain oxidative phosphorylation and act as a direct cardio-protectant through ATP production. In 1974, the Japanese Government has approved CoQ-10 for the treatment of cardiovascular disease, leading to its use by more than 12 million Japanese adults today. In addition, the use of CoQ-10 has also been widely advocated by healthcare professionals throughout the United States and Europe. [Mortensen S A, et al. Coenzyme Q10—clinical benefits with biochemical correlates suggesting a scientific breakthrough in the management of chronic heart failure. Int J Tiss Reac 12:155-162, 1990; Mortensen S A. Perspectives on therapy of cardiovascular diseases with coenzyme Q10 (ubiquinone). Clin Investig 71:S116-123, 1993].

Another widespread replenishment of CoQ-10 is in the clinical management of hypertension associated with deficiencies of succinate dehydrogenase and CoQ-10 reductase activity. Accordingly, reversal of CoQ-10 deficiency by dietary replenishment seems to control hypertension with reductions in systolic and diastolic blood pressure. [Greenberg S, Frishman W H. Coenzyme Q10—A new drug for cardiovascular disease. J Clin Pharmacol 30:596-608, 1990; Yamagami T, Shibata W, Folkers K. Bioenergetics in clinical medicine. Studies on coenzyme Q10 and essential hypertension. Res Commun Chem Pathol Pharmacol 11:273-288, 1975; Yamagami T, Shibata W, Folkers K. Bioenergetics in clinical medicine. VIII. Administration of coenzyme Q10 to patients with essential hypertension. Res Commun Chem Pathol Pharmacol 14:721-727, 1976].

Yet another common application of CoQ-10 is as an active adjuvant to rectify (balance) coenzyme deficiency that builds-up during long-term usage of certain medications. Lipid-lowering drugs ("statins") such as lovastatin, simvastatin, pravastatin and gemfibrozil cause a decrease in serum CoQ-10 levels, which might predispose serious cardiovascular conditions. Therefore, it is advisable to use CoQ-10 supplement with prescription of statins, to protect individuals from risks associated with cardiac dysfunction. Beta-blockers (drugs that slow down heart rate and lower blood pressure) could also decrease the endogenous CoQ-10 levels by inhibition of CoQ-10-dependent enzymes. Also, certain oral hypoglycemic agents such as glyburide, acetohexamide, and tolazamide could decrease plasma CoQ-10 levels. CoQ-10 supplementation has been reported to reduce insulin requirements in diabetes mellitus. Therefore, diabetic patients taking CoQ-10 might require dosage adjustments of hypoglycemic agents. [Kaikkonen J, et al. Determinants of plasma coenzyme Q10 in humans. FEBS Lett 443:163-166, 1999; Thibault A, et al. Phase I study of lovastatin, an inhibitor of the mevalonate pathway, in patients with cancer. Clin Cancer Res 2:483-491, 1996; Pepping J. Coenzyme Q. Am J Health-System Pharm 56:519-521, 1999; Kishi T, et al. Bioenergetics in clinical medicine. Studies on coenzyme Q and diabetes mellitus. J Med 7:307-321, 1976].

Generally, individuals intending to boost physiological CoQ-10 levels consume this coenzyme as a dietary supplement in various forms, such as soft gels (most popular delivery format), capsules, tablets, powders or liquids. Regular doses of 30-60 mg/day (approximately 1 mg/kg of body weight) are generally recommended to prevent CoQ-10 deficiency and to maintain normal serum concentrations of 0.7-1.0 μg/mL. Therapeutic doses of 100-200 mg/day are recommended in the treatment of chronic heart disease. These higher doses may achieve serum concentrations of 2.0-3.0 μg/mL, in order to provide a positive impact on cardiovascular health. Divided doses have also been used to minimize adverse effects (if any) when the supplementation exceeds 100 mg/day. [Pepping J. Coenzyme Q10. Am J Health-Syst Pharm 56:519-521, 1999].

The metabolic fate and physiological turnover of CoQ-10 supplemented through the diet has not been fully elucidated. Early studies have indicated that peak levels of CoQ-10 in the plasma are attained within 5-10 hours following oral administration. After intestinal absorption, CoQ-10 is initially sequestered by chylomicrons, transferred to the liver and incorporated into the very low density lipoproteins (VLDL). The elimination half-life of CoQ-10 is approximately 34 hours and its excretion is primarily through the biliary tract. [Greenberg S, Frishman W H. Coenzyme Q10: a new drug for cardiovascular disease. J Clin Pharmacol 30:596-608, 1990].

Reduced bioavailability due to poor intestinal absorption is a major limitation to use CoQ-10 as a health supplement. Several factors in the gastrointestinal milieu such as inflammatory conditions, pH, and mucosal brush border status markedly influence the CoQ-10 absorption. Accordingly, more than 60% of the orally administered CoQ-10 is excreted in the feces.

Isoprenoid side-chain in the quinone structure makes CoQ-10 an extremely lipophilic molecule. Therefore, when administered in the form of an oil solution or some kind of water and/or oil suspension or emulsion, lipophilic compounds usually show a poor bioavailability, which results in low concentration and a long build-up time of the compound in the systemic circulation. Therefore, it is highly critical to develop effective methods to overcome this set back, which is inherent to CoQ-10.

Several attempts to reduce the dosage quantities, and enhance bioavailability of CoQ-10 with solubility-enhancing agents have been reported. For instance, U.S. Pat. No. 4,824,669 describes a soft gel capsule with CoQ-10 and at least one vegetable oil carrier. This formula claims to increase blood basal levels of CoQ-10 to 2.5 g/mL in comparison to 1.6 g/mL from an equivalent 100 mg dose of a dry powder formulation. U.S. Pat. No. 4,483,873 discloses aqueous solutions of hydrogenated lecithin to increase CoQ-10 bioavailability. U.S. Pat. No. 6,045,826 discloses water-soluble compositions of CoQ-10 with a single solubilizing agent containing both hydrophobic and hydrophilic moieties. U.S. Pat. Nos. 6,056,971 and 6,441,050 disclose methods to solubilize CoQ-10 in a softgel, by mixing with an edible polyhydric alcohol solvent. U.S. Pat. No. 6,300,377 teaches about a CoQ-10 composition that omits polyhydric alcohol, but includes other agents to help improve solubility, including a glyceryl ester molecule having one to three $C_2$ to $C_7$ acyl groups. U.S. Pat. No. 6,623,734 utilizes medium chain triglycerides or "GelOil SC (a thixatropic gelatine composition)" as carriers. U.S. Pat. No. 6,740,338 discloses a method to use a lipid-soluble reducing agent (eg. ascorbyl palmitate) to maintain CoQ-10 in reduced state as ubiqinol for enhanced bioavailability.

While many patents and different formulations claim increased bioavailability of CoQ-10, the data supporting these claims are often inconclusive. Despite the continuing efforts to enhance the chemical solubility, the issue of limited intestinal diffusion of CoQ-10 continues to plague its applications as a broad-spectrum health supplement. There is a global necessity to develop an effective system to boost the intestinal assimilation of CoQ-10, preferably by active transport mechanisms, to augment its bioavailability for various cellular functions.

The physiological consequence of CoQ-10 supplementation intended for cardiovascular support also needs an in-depth scientific evaluation. In other words, the structure-function compatibility of a CoQ-10 replenishment to generate high cellular energy (strong "exogenous functional boost") with a compromised cardiovascular matrix (weak "endogenous structural frame") such as in an elderly or diseased individual requires a careful pharmacological assessment.

It should be noted that the physiological levels of CoQ-10 decline with age, in order to establish a 'natural balance' between the bioenergetics and the cellular degeneration. Plasma CoQ-10 concentration reach peak levels at 19-21 years of age and plummets down to 65% by age 80. CoQ-10 deficiency is prevalent among patients with congestive heart failure (CHF), cardiomyopathy, and chronic obstructive pulmonary disease (COPD). Certain individuals may experience premature decline in CoQ-10 levels or suffer from a disorder or condition that hinders CoQ-10 synthesis. Such CoQ-10 deficiencies may develop with long-term drug use while treating blood disorders such as hyper-lipidemia (eg. statins to reduce cholesterol), hypertension (eg. beta-blockers to control blood pressure), and diabetes (eg. sulfonylurea-type to regulate blood sugar). All of the above clinical conditions are manifested by severe fatigue and lack of energy.

In order to establish a physiological balance between cardiovascular condition and cellular energy requirements, it is necessary to promote regeneration of cardiac muscles ("angiogenesis") and reinforce the vascular tissue ("vasculogenesis"). Therefore, the boosting of cellular energy with CoQ-10 supplementation, especially during the management of cardiovascular health, it becomes critically important that the underlying cellular-matrix is strengthened using in vivo stimulants of angiogenesis and vasculogenesis. This fundamental approach of 'structure-functional' balancing of CoQ-10 for human health applications has neither been addressed nor reduced to practice by nutritional or pharmaceutical industry so far.

The present invention provides a novel solution that could significantly influence the global perspective of CoQ-10 applications for human and animal health.

SUMMARY OF THE INVENTION

Embodiments of the invention provide formulations that provide effective assimilation of CoQ-10 while supporting angiogenesis and vascular generation, particularly in cardiac tissue.

Embodiments of the invention are directed to compositions which include at least one of CoQ-10, angiogenin (AGN), and one or more metal-transport proteins. Preferably, the metal-transport protein is combined with an anionic compound such as a carbonate, a bicarbonate, or a carbonated liquid. Most preferably, the anionic compound is bicarbonate.

In preferred embodiments, the metal-transport protein is one or more of lactoferrin (LF), ovotransferrin or transferrin. Most preferably, the metal-transport protein is lactoferrin.

In preferred embodiments, the amount of CoQ-10 is from 0.1 to 90% by weight and the amount of metal-transport protein is from 0.1 to 90% by weight.

In preferred embodiments, the metal-transport protein such as lactoferrin is complexed to a metal such as copper, iron, zinc, manganese, chromium, aluminum or gallium. Most preferably, the composition includes lactoferrin complexed to copper.

In preferred embodiments, the ratio of metal-transport protein:AGN ranges between 100:1 to 1:100. More preferably, the ratio of metal-transport protein:AGN ranges between 9:1 to 3:1.

In preferred embodiments, the composition may also include an oil, or other suspending agent, flavoring, coloring agents or combinations thereof. Preferably, the oil is one or more selected from seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, palm oil, rapeseed oil, palm kernel oil, lupin oil, coconut oil, flaxseed oil, or evening primrose oil.

In preferred embodiments, the composition also includes phospholipids, antioxidants, vitamins, amino acids, proteins, essential minerals, lecithin and derivatives thereof or combinations thereof. More preferably, the phospholipid is one or more selected from Docosahexaenoic acid (DHA), phosphatidyl glycerol, phosphatidyl inositol, phosphatidyl serine, phosphatidyl choline, phosphatidyl ethanolamine, phosphatidic acids, ceramides, cerebrosides, sphingomyelins and cardiolipins. More preferably, the vitamin is one or more selected from vitamin A, thiamine, niacinamide, pyridoxine, riboflavin, cyanocobalamin, biotin, pantothenic acid, vitamin C, vitamin D, vitamin E, vitamin K and folic acid. More preferably, the mineral is one or more selected from iron, calcium, magnesium, sodium, potassium, copper, chromium, zinc, molybdenum, iodine, boron, selenium, manganese, derivatives thereof and combinations thereof. More preferably, lecithin is present in an amount of 10% to 60% by weight.

In preferred embodiments, the composition also includes L-carnitine, acetyl-L-carnitine or propionyl L-carnitine in an amount of 1% to 50% by weight.

In preferred embodiments, the composition also includes a viable or a non-viable probiotic which is *L. acidophilus, L. amylovorus, L. animalis, L. bavaricus, L. brevis, L. bulgaricus, L. casei* spp. *casei, L. casei* spp. *rhamnosus, L. crispatus, L. delbrueckii* spp. *lactis, L. eichmanni, L. fermentum, L. helveticus, L. jensenii, L. kefir, L. paracasei, L. pentosus, L. plantarum, L. reuteri, L. salivarius, L. sake, Leu. cremoris, Leu. lactis; B. adolescentis, B. animalis, B. bifidum, B. breve, B. infantis, B. longum*, and *B. thermophilum; Ped. acidilactici, Ped. pentosus, Pep. assacharolyticus, Pep. productus; Pro. acidipropionici, Pro. freudenreichii, Pro. jensenii, Pro. theonii, Strep. cremoris, Strep. faecium, Strep. lactis, Strep. raffinolactis* or *Strep. thermophilus*.

Embodiments of the invention are directed to methods of preparing a LF:AGN premix which includes one or more of the following steps:

isolating a LF-enriched fraction from a dairy, a non-dairy or a recombinant source;

isolating an AGN-enriched fraction from a dairy, a non-dairy or a recombinant source;

combining the LF-enriched fraction with the AGN-enriched fraction;

freeze-drying or spray-drying the combined fractions; and milling the freeze-dried or spray-dried combined fractions to obtain a LF:AGN premix.

Embodiments of the invention are directed to LF:AGN premix compositions, including those produced by the above method.

In preferred embodiments, the ratio of LF to AGN is 9:1. More preferably, the ratio of LF to AGN is 6:1. Yet more preferably, the ratio of LF to AGN is 3:1.

Embodiments of the invention are directed to methods of maintaining good health or treating a disease condition by administering any of the compositions described above to an individual.

A preferred embodiment is directed to a formulation for vascular health which includes CoQ-10, angiogenin, at least one metal-transport protein, and at least two of the following ingredients: acetyl L-carnitine, vitamin B6, Vitamin E, Selenium, Copper and Flaxseed oil.

A preferred embodiment is directed to a formulation for sports nutrition which includes CoQ-10, angiogenin, at least one metal-transport protein, and at least two of the following ingredients: one or more B vitamins, vitamin C, vitamin E, glutamine, taurine, N-acetyl-creatine, N-acetyl-cysteine, one or more L amino acids, acetyl L-carnitine, sodium and potassium salts, selenium, magnesium, copper, and chromium.

A preferred embodiment is directed to a formulation to promote tissue recovery after exercise which includes CoQ-10, angiogenin, at least one metal-transport protein and at least two of the following ingredients: soy lecithin, vitamin B6, vitamin E, selenium, copper, L-taurine, N-acetyl creatine, Dehydroepiandrosterone (DHEA), and one or more amino acids.

Embodiments of the invention are directed to a protein powder, a sports beverage, a carbonated beverage and/or a meal replacement health bar which include CoQ-10, angiogenin, at least one metal-transport protein or any of the formulations as described. A preferred embodiment is directed to a method of preparing a tonic to support muscle building by mixing a protein powder containing CoQ-10, angiogenin, at least one metal-transport, or one of the formulations described with a food or beverage.

A preferred embodiment is directed to a formulation for reducing or preventing vascular plaque which includes CoQ-10, angiogenin, at least one metal-transport protein and at least two of the following ingredients: pantethine, one or more plant antioxidants, L-carnitine, and red yeast rice.

A preferred embodiment is directed to a formulation for the treatment of symptoms of premenstrual syndrome which includes CoQ-10, angiogenin, at least one metal-transport protein and at least two of the following ingredients: γ-linolenic acid, evening primrose oil, chaste tree extract, one or more B vitamins, folic acid, biotin, calcium and magnesium.

A preferred embodiment is directed to a formulation for the treatment of day-time symptoms of perimenopause which includes CoQ-10, angiogenin, at least one metal-transport protein and at least two of the following ingredients: vitamin B6, vitamin E, vitamin C, selenium, calcium, magnesium, potassium, black cohosh, and red clover. In a preferred embodiment, day-time symptoms of perimenopause are treated by administering an effective amount to an individual in need thereof.

A preferred embodiment is directed to a formulation for treating night-time symptoms of perimenopause which includes CoQ-10, angiogenin, at least one metal-transport protein and at least two of the following ingredients: vitamin B5, vitamin E, vitamin C, selenium, calcium, magnesium, potassium, gamma-oryzanol, L-theanine, and valerian root. In a preferred embodiment, night-time symptoms of perimenopause are treated by administering an effective amount to an individual in need thereof.

A preferred embodiment is directed to a formulation for treating symptoms of menopause which includes CoQ-10, angiogenin, at least one metal-transport protein and at least two of the following ingredients: α-linolenic acid, vitamin D, S-adenosylmethionine, methylsulfonylmethane, calcium, magnesium and chromium.

A preferred embodiment is directed to a vaginal suppository for treating an infection of bacterial, fungal or parasitic origin which includes CoQ-10, angiogenin, at least one metal-transport protein and a probiotic microorganism.

A preferred embodiment is directed to a formulation for bone health which includes CoQ-10, angiogenin, at least one metal-transport protein and at least two of the following ingredients: chondroitin sulfate, glucosamine sulfate, methylsulfonylmethane, S-adenosylmethionine, dimethylglycine, and cerasomal-cis-9-cetylmyristoleate.

A preferred embodiment is directed to a formulation for oral hygiene which includes CoQ-10, angiogenin, and at least one metal-transport protein.

A preferred embodiment is directed to a formulation for topical use in an acceptable carrier which includes CoQ-10, angiogenin, and at least one metal-transport protein.

A preferred embodiment is directed to a formulation for decreasing the frequency of migraine attack which includes CoQ-10, angiogenin, at least one metal-transport protein, magnesium and riboflavin.

A preferred embodiment is directed to a formulation for enhancing male virility which includes CoQ-10, angiogenin, at least one metal-transport protein and at least two of the following ingredients: damiana extract, sarsaparilla extract, saw palmetto, and acetyl-L-carnitine.

A preferred embodiment is directed to a formulation for increasing female libido which includes CoQ-10, angiogenin, at least one metal-transport protein and at least two of the following ingredients: lysozyme, cranberry extract, L-theanine, Echinacea, acetyl-L-carnitine, and tyrosine.

A preferred embodiment is directed to a formulation for brain health and stress management which includes CoQ-10, angiogenin, at least one metal-transport protein and at least two of the following ingredients: phosphatidyl serine, phenylalanine, one or more B vitamins, vitamin E, taurine, choline, copper and chromium.

A preferred embodiment is directed to a formulation for colon cleansing which includes CoQ-10, angiogenin, at least one metal-transport protein and at least two of the following ingredients: at least one probiotic, cascara sagrada, peppermint oil, gingerol oil, fennel oil, and *chlorella*.

A preferred embodiment is directed to a formulation for liver cleansing which includes CoQ-10, angiogenin, at least one metal-transport protein, milk thistle and dandelion.

A preferred embodiment is directed to a formulation for blood cleansing which includes CoQ-10, angiogenin, at least one metal-transport protein and at least two of the following ingredients: burdock root extract, rosemary leaf extract, red clover extract and yarrow.

A preferred embodiment is directed to a powdered drink formulation which includes CoQ-10, angiogenin, at least one metal-transport protein, golden seal, and echinacea. More preferably, the powdered drink formulation also includes one or more selected from ginger root extract, vitamin C, peppermint, grapefruit seed extract, licorice root extract, cranberry extract, elder, and L-theanine.

Embodiments of the invention are directed to methods of treating a an age-related or physiological Coenzyme Q-10 deficiency, and/or a deficiency condition resulting from long-term drug use in the clinical management of hypertension, hyperlipidemia and diabetes mellitus, by administering a composition which includes CoQ-10, angiogenin, and at least one metal-transport protein at an effective dosage to an individual in need thereof.

Embodiments of the invention are directed to a method of soft gel encapsulation of compositions which include CoQ-10 and angiogenin, where the gel material is one or more selected from bovine gelatin, fish gelatin, lecithin, fatty acids, oils and waxes.

Further aspects, features and advantages of this invention will become apparent from the detailed description of the preferred embodiments which follow.

DETAILED DESCRIPTION OF THE PREFERRED EMBODIMENT

While the described embodiment represents the preferred embodiment of the present invention, it is to be understood that modifications will occur to those skilled in the art without departing from the spirit of the invention. The scope of the invention is therefore to be determined solely by the appended claims.

One object of the present invention is to provide a natural delivery system for active transport of orally administered CoQ-10 across the intestinal mucosa. A further object of the present invention is to provide a high degree of CoQ-10 bio-availability in the blood circulation for its multi-functional assimilation in the body.

Another object of the present invention is to provide an effective cardiovascular reinforcement system to cope with the cellular energy synthesis anticipated by the bio-available CoQ-10 supplemented by oral administration.

The objectives of the present invention have been accomplished by incorporating into the CoQ-10 formulations, two nutraceutical milk proteins, namely, "lactoferrin (LF)", the body's own transportation system and "angiogenin (AGN)", the body's own growth factor that regulates regeneration of vascular tissue.

Lactoferrin (LF) is the fundamental glycoprotein that plays a key role in the transport and absorption of nutrients into the blood stream, crossing the intestinal mucosal barrier. Accordingly, LF is equipped with unique molecular structure and a classic functional mechanism for active transport and physiological mobilization of iron, zinc, copper, manganese, chromium, aluminum, gallium and several other vital nutrients for metabolic assimilation. Furthermore, LF also elicits a powerful protective role in the intestinal tract by eliminating harmful pathogens, toxic chemicals, heavy metals, and free radicals. Specific receptors in the human duodenal brush border are involved in promoting LF interaction and function during the elemental absorption and nutrient transport. These LF-binding receptors exist relatively at a high density (about 4 billion sites/microgram) on the human intestinal brush-border membrane to facilitate uninterrupted active transport and processing of nutrients into the circulatory system. [Naidu A S. Lactoferrin—Natural Multifunctional Antimicrobial, CRC Press/Boca Raton, pp. 1-86, 2000; Cox et al., Iron-binding proteins and influx of iron across the duodenal brush border. Evidence for specific lactotransferrin receptors in the human small intestine. Biochem Biophys Acta 588: 120-8, 1979; Kawakami H, Lonnerdal B, Isolation and function of a receptor for human lactoferrin in human fetal intestinal brush-border membranes. Am J Physiol 261:G841-6, 1991].

In general, low molecular weight molecules such as ions and metabolites (possibly CoQ10) cross the gut lumen through "passive diffusion processes" facilitated by membrane channels in the lumen. Whereas, orally administered LF could pass into the systemic circulation as an intact molecule by two distinct pathways: i) by non-selective transcytosis and ii) by specific receptor-mediated transcytosis. LF is known to bind and potentiate active transport of several molecules across membrane barriers. The pharmaco-kinetics of LF absorption in the intestinal tract is fast and reaches a peak level in plasma within 2-h. Furthermore, LF is also rapidly eliminated from the plasma with a mean fractional catabolic rate of 5.7/day, by liver and spleen. [Takeuchi T, et al. Evidence of lactoferrin transportation into blood circulation from intestine via lymphatic pathway in adult rats. Exp Physiol 89:263-270, 2004].

Therefore, presence of supplemented LF in the intestinal milieu, either in free form or complexed to CoQ-10 could facilitate an active transport of several low molecular weight molecules across the intestinal brush border epithelia. The present invention takes advantage of this basic principle in facilitating the transport of CoQ-10 across the intestinal lumen into the blood stream. [Naidu A S. Arnold R R. Lactoferrin interaction with Salmonellae potentiates the antibiotic susceptibility in vitro. Dign Microbiol Infect Dis 20:69-75, 1994].

LF is a 79-kDa glycoprotein present in every mucosal secretion of the human body. LF occurs in two major reservoirs, a circulatory pool stored in the neutrophils and a stationary pool covered on the mucosal surfaces. In the neutrophils, LF is associated with the secondary (specific) granules at a concentration of about 15 µg/$10^6$ cells and is released isochromously with other lysosomal proteins into the plasma during phagocytosis. The concentration of LF in human plasma is about 0.2 to 1.5 µg/mL, the values are comparatively lower in women than in men. Notably, LF is a powerful nutraceutical with well established antimicrobial, antioxidant, anti-inflammatory, immuno-modulatory, and prebiotic properties. Furthermore, the iron-binding property of LF is known to play a vital role in the CoQ-10/Cytochrome (iron-containing compounds)-mediated bioenergetic pathways [review: Naidu A S. Ultra-cleansing of lactoferrin—nutraceutical implications. AgroFood Industry hi-tech 16:7-13, 2005].

Angiogenesis and vasculogenesis are two primary pathways in the development and maintenance of mammalian health. The angiogenic role is to supply and support tissue with ample vasculature, thus providing a route of access for the transportation of essential nutrients, including oxygen and the removal of metabolic waste in a sustained manner. Angiogenesis is a strictly regulated, multi-step process that occurs during normal physiology such as wound healing, pregnancy, and development.

In preferred embodiments, the coenzyme Q-10 compositions include an agent that promotes angiogenesis and/or vasculogenesis. Such agents include, but are not limited to angiogenin, vascular endothelial growth factor (VEGF), fibroblast growth factor-acidic (FGF-a), fibroblast growth factor-basic (FGF-b), tumor necrosis factor (TNF)-$\alpha$, and transforming growth factor (TGF)-$\alpha/\beta$. In a preferred embodiment, the angiogenic/vasculogenic agent is angiogenin.

Angiogenin (AGN) has been shown to be a key mediating factor in the underlying cascade of chemical events leading to angiogenesis, which makes it a very important precursor molecule for both muscle development and vascular generation. AGN is a 14-kDa, basic heparin-binding protein and a member of the pancreatic ribonuclease superfamily. AGN resembles pancreatic ribonuclease A; their amino acid sequences are about 35% identical, including the active site residues. [Strydom D J. The angiogenins. Cell Mol Life Sci 54:811-824, 1998; Acharya B, et al. Crystal structure of human angiogenin reveals the structural basis for its functional divergence from ribonuclease. Proc Natl Acad Sci USA 91:2915-2919, 1994].

AGN is present in milk and circulates in human plasma at a concentration of about 0.3 µg/mL. Its turnover rate is very fast, with a half-life <5 min. AGN can induce most of the events necessary for the formation of new blood vessels. It binds avidly to endothelial cells and stimulates cell migration and invasion. AGN promotes cell proliferation and differentiation; mediates cell adhesion and activates cell associated proteases; and also induces plasminogen activator and thereby, the plasmin system promoting migration and tubular morphogenesis of endothelial cells. Exogenous AGN is transported into the nucleus of endothelial cells. The nuclear translocation results in accumulation of the AGN in the nucleolus. Transportation of AGN from the cell surface into the nucleus and subsequently to the nucleolus is critical for its angiogenic activity. The import of AGN from the cytosol to the nucleus is signal-dependent, carrier mediated and energy-dependent, active transport process. [Hu G F, Riordan J F, Vallee B L. A putative angiogenin receptor in angiogenin-responsive human endothelial cells. Proc Natl Acad Sci USA 94:2204-2209, 1997; Moroianu J, Riordan J F. Nuclear translocation of angiogenin in proliferating endothelial cells is essential to its angiogenic activity. Proc Natl Acad Sci USA 91:1677-1681, 1994].

The present invention relates to novel compositions comprising effective amounts of CoQ-10. In preferred embodiments, CoQ-10 is provided in a composition that also includes an agent that promotes angiogenesis and/or vasculogenesis. In preferred embodiments, the agent to support angiogenesis and/or vasculogenesis is angiogenin. Effective amounts of angiogenin in the formulation reinforce the cardiovascular framework to cope with the bioenergetic functions of CoQ-10 supplementation. In preferred embodiments, the composition includes an amount of LF effective to bind and transport CoQ-10 into the blood stream, preferably across the intestinal mucosa.

Compositions according to the present invention may be used for treatment of cardiovascular ailments and diseases such as congestive heart failure, cardiomyopathy; for supportive supplementation of long-term medications in the management of hypertension, hyperlipidemia, diabetes, and chronic fatigue syndrome; mitochondrial diseases including mitochondrial encephalomyopathy, lactic acidosis, and stroke-like symptoms, Kearns-Sayre syndrome and Alper' disease;

Definition of Terms

Coenzyme Q10: As used herein, "coenzyme Q10" or "CoQ-10" refers to fat-soluble quinone (chemical name: 2,3-dimethoxy-5-methyl-6-decaprenyl-1,4-benzoquinone; CAS registry no. 303-98-0), structurally similar to vitamin K. Coenzyme Q10 is also known by the names ubiquinone, ubidecarenone, neuquinone and vitamin-Q. Coenzyme Q10 used herein also includes different forms of CoQ-10, for example: reduced CoQ-10, semi-reduced CoQ-10, and genetically or chemically modified CoQ-10. As used herein, coenzyme Q10 used herein also refers to "coenzyme Q10 blends" described in the present invention.

Coenzyme Q10 blend: As used herein, "coenzyme Q10 blend" or CoQ-10 blend" refers to mixtures of CoQ-10 with LF and AGN; all combined or individually at varying ratios, eg. CoQ-10, LF and AGN; CoQ-10 and LF; as well as, CoQ-10 and AGN.

Metal-transport proteins: As used herein, "metal-transport proteins" refers to compounds belonging to transferrin super-family. Lactoferrin, transferrin, ovo-transferrin (synonym: conalbumin) and melano-transferrin.

Lactoferrin: As used herein, "lactoferrin", or "LF" refers to various protein preparations and forms, including but not limited to, lactoferrin-(tcr) (as described in Naidu U.S. Pat. Appl. No. 20050197495, published Sep. 8, 2005), freely-dispersed native (fdn)-lactoferrin which includes metal-saturated (holo), partially saturated and metal-free (apo) forms of LF. The LF-bound metal is preferably copper, and other bound metals include zinc, iron, manganese, chromium, aluminum and gallium. The term LF further refers to fully and partially glycosylated polypeptide chains of LF, incomplete polypeptide chains including half-molecules comprising C- and N-terminus lobes of LF. The term LF categorically excludes aggregated-LF and immobilized (Im)-LF forms (as described in Naidu U.S. Pat. No. 6,172,040 B1, issued Jan. 9, 2001) that are devoid of any (fdn)-LF.

Freely-dispersed native lactoferrin: As used herein, "freely-dispersed native (fdn)-lactoferrin" or "(fdn)-LF" refers to isolated LF protein molecules free of auto-aggregation or polymerization and free from binding or immobilization to other substrates.

Angiogenic stimulators: As used herein, "angiogenic stimulators" refers to growth factors that stimulate neogenesis and regeneration of vascular tissue including the cardiac muscles. These growth factors include, but not limited to, angiogenin, vascular endothelial growth factor (VEGF), fibroblast growth factor-acidic (FGF-a), fibroblast growth factor-basic (FGF-b), tumor necrosis factor (TNF)-α, and transforming growth factor (TGF)-α/β.

Angiogenic inhibitors: As used herein, "angiogenic inhibitors" refers to physiological regulators that inhibit biosynthesis of vascularization process. These regulatory compounds include, but not limited to angiostatin, thrombospondin-1 and interferon-α/β, platelet factor factor-4, 16 kDa N-terminal fragments of prolactin, and endostatin.

Angiogenin: As used herein, "angiogenin" or "AGN" refers to an angiogenic-stimulating factor, which is also 14-kDa heparin-binding protein that occurs in most cells, also present in various biological fluids such as plasma and milk.

Phospholipid: As used herein, "phospholipids" refers to phosphated fatty acids, including but not limited to phosphatidyl glycerol, phosphatidyl inositol, phosphatidyl serine, phosphatidyl choline, phosphatidyl ethanolamine, as well as phosphatidic acids, ceramides, cerebrosides, sphingomyelins and cardiolipins.

Antioxidant: As used herein, "antioxidant" refers to synthetic or natural substances that prevent or delay the oxidative deterioration of a compound. Exemplary antioxidants include tocopherols, flavonoids, catechins, superoxide dismutase (SOD), lecithin, gamma oryzanol; vitamins, such as vitamins A, C (ascorbic acid) and E and beta-carotene; natural components such as carnosol, carnosic acid and rosmanol found in rosemary and hawthorn extract, proanthocyanidins (PAC) such as those found in grapeseed or pycnogenol found in maritime pine bark extract.

Catechin: As used herein, "catechin" refers to polyphenolic compounds found in many plants, green tea in particular, that could protect the body from several diseases. These compounds include but not limited to epi-gallo catechin gallate (EGCG), epi-gallo catechin (EGC) and epi-catechin (EC).

Probiotic: As used herein, "probiotic" refers to nutritional supplements of beneficial intestinal bacteria intended to re-colonize the intestines to promote digestive health. A probiotic is also described as a preparation or a product containing viable, defined microorganisms with or without other substances in sufficient numbers, which improve or alter the microflora or their properties (by implantation or colonization) in a compartment of the host and thereby exert beneficial health effects in the host. The commonly used probiotic microorganisms include but not limited to bacterial genus *Lactobacillus, Lactococcus*, and *Bifidobacteria*.

Effective amount: As used herein, "effective amount" refers to describe concentrations or amounts of compounds according to the present invention which may be used to produce a favorable result, whether that result relates to a composition's therapeutic or physiological effect in compositions according to the present invention.

Daily Value: As used herein, "Daily Value" or "% DV" refers to describe a term on food labels based on the RDA (Recommended Dietary Allowance) designed to help consumers use food label information to plan a healthy diet. The Daily Value serves as a basis for declaring on the label the percent of the DV for each nutrient that a serving of the food provides.

Oral administration: As used herein, "oral administration" refers to any form of delivery of an agent or composition thereof to a subject wherein the agent or composition is placed in the mouth of the subject, whether or not the agent or composition is swallowed. Thus, 'oral administration' includes buccal and sublingual as well as esophageal administration. Absorption of the agent can occur in any part or parts of the gastrointestinal tract including the mouth, esophagus, stomach, duodenum, ileum and colon.

Plant antioxidants: As used herein, "plant antioxidant" has its usual and customary meaning and includes carotenoids such as lycopene and lutein.

Embodiments of the invention provide physiologically deliverable, compositions comprising effective amounts of CoQ-10. More preferably, the CoQ-10 compositions of the preferred embodiments include LF and/or AGN, and optionally one or more bio-active agents. In a most preferred embodiment, composition include CoQ-10, angiogenin and LF. Compositions of the invention also may include others components, such as oils, and other carriers. In preferred embodiments, delivery of the CoQ-10 compositions is by the oral route;

In the present invention, the amount of CoQ-10 that is included in a mixed composition depends upon the form of LF and may range from about 0.1% to 90% by weight, preferably about 5% to 50% by weight, and most preferably about 10% to 20% by weight.

In an embodiment of the present invention, suitable CoQ-10 is available from a variety of commercial sources (Alchem International from India, Daewoog from Korea, Xi'an Yier Hi-Tech Industry and Terio Corporation from China, and Kaneka Corporation from Japan). These suppliers may produce CoQ-10 by different methods, including but not limited to controlled microbial fermentation, direct chemical extraction from animal tissue (eg. beef heart) or higher plants (eg. tobacco, followed by synthetic alteration of the side chain). Some differences may exist between CoQ-10 prepared from systems comprising prokaryotic and eukaryotic biosynthesis. CoQ-10 from fermentation technology may use an array of microbial systems including bacteria (eg. *Gluconobacter suboxydans, Agrobacterium tumefaciens, Sporidiobolus ruineniae*), yeast (eg. *Schizosaccharomyces pombe*), or fungi (eg. *Rhodotorula minuta, Leucosporidium scotti, Aspergillus clavatus, Bulleromyces albus*).

In the present invention, the effective amounts of LF in a mixed composition may range from about 0.1% to 90% by weight, preferably about 1% to 25% by weight, and most preferably about 5% to 10% by weight.

Suitable lactoferrin is available from various commercial sources (N-terminus or Glanbia from USA, Tatua or Fonterra from New Zealand, MG Nutritionals from Australia, Morinaga Milk Company from Japan, DMV International from the Netherlands). Suitable lactoferrin can be isolated from dairy sources including colostrum, milk, and whey; milk serum from humans, cows, buffalos, horses, sheep, pigs or camels. Additionally the ultra-cleansed lactoferrin preparation can be purified from recombinant sources and genetically-modified organisms (GMOs).

In an embodiment of the present invention, in a mixed composition, LF may be partially chelated (covalently bound) to a metal ion including but not limited to iron, zinc, copper, manganese, chromium, aluminum and gallium; preferably bound to iron, zinc and copper, most preferably bound to copper.

In another embodiment of the present invention, LF-copper metal complexes are prepared by adding LF protein with citrated copper sulfate solution containing excess of citric acid (pH 2.5; 60 mol citrate: 1 mol copper). After incubation for 10 min, pH is raised to 7.0 with 0.1M NaOH. Sodium bicarbonate is added in excess (2 mol bicarbonate: 1 mol copper) and any unbound copper is removed (if necessary) by gel filtration.

In another embodiment of the present invention, LF may be formed into a complex with CoQ-10 by physical and/or chemical interactions. LF and CoQ-10 may be complexed together directly or they may be complexed by means of an appropriate bifunctional reagent. The LF:CoQ-10 complex may be a covalent or non-covalent complex. A non-covalent complex may be formed by means of electrostatic interactions which may be enhanced by inclusion of appropriate buffers and/or salts. In one preferred embodiment, Cu-LF is complexed with either CoQ-10 or AGN.

In the present invention, the effective amounts of AGN in a mixed composition may range from about 0.1% to 90% by weight, preferably about 0.5% to 25% by weight, and most preferably about 1% to 10% by weight.

In yet another embodiment of the present invention, LF can be mixed with AGN, directly during the chemical extraction-isolation process, either by co-eluting both protein fractions under similar chromatographic conditions, or by combining both the fractions at pre-determined ratios after the isolation process. In a preferred embodiment, LF and AGN are co-isolated from milk by a purification scheme that provides a fraction enriched in both LF and AGN. In a most preferred embodiment, LF and AGN are isolated from milk separately, but then recombined at the desired ratio before a lyophillization step. Lyophillization may be carried out by any means known in the art, preferably by freeze-drying or spray-drying. Once the lyophillized powder containing LF and AGN is obtained, the powder can be milled to provide a LF:AGN premix powder at the desired ratio of LF and AGN. Alternatively, LF and AGN can be separately isolated and dried to a purified powder. The purified LF and AGN powders can then be mixed together to provide a LF:AGN premix of the desired ratio.

In the present invention, the ratios of LF:AGN premix may range between 100:1 to 1:100, preferably 10:1 to 1:10, most preferably 6:1 to 3:1, respectively.

Suitable AGN can be isolated from dairy sources including colostrum, milk, whey and milk serum from humans, cows, buffalos, horses, sheep, pigs or camels. Additionally, AGN also can be purified from other biological fluids from animals (eg. blood), recombinant sources and genetically-modified organisms (GMOs).

In an embodiment of the present invention, AGN may be combined with copper and zinc, preferably copper. Direct interaction of copper and zinc could increase AGN binding to endothelial cells. Since copper is a known modulator of angiogenesis in vivo, it may be engaged in the regulation of AGN activity. [Soncin F, et al. Interaction of human angiogenin with copper modulates angiogenin binding to endothelial cells. Biochem Biophys Res Commun 236:604-610, 1997].

In another embodiment of the present invention, AGN may be formed into a complex with LF by physical and/or chemical interactions. AGN and LF may be complexed together directly or they may be complexed by means of an appropriate bifunctional reagent. A non-covalent complex may be formed by means of electrostatic interactions which may be enhanced by inclusion of appropriate buffers and/or salts.

In yet another embodiment of the present invention, AGN may be formed into a complex with CoQ-10 by physical and/or chemical interactions. AGN and CoQ-10 may be complexed together directly or they may be complexed by means of an appropriate bifunctional reagent. A non-covalent complex may be formed by means of electrostatic interactions which may be enhanced by inclusion of appropriate buffers and/or salts. AGN contains a signal peptide, called the nuclear localization sequence (NLS) in its amino acid sequence that mediates its import into the nucleus. NLS is located in the N-terminal region of human AGN comprised of the amino acid residues from 31-35, i.e. RRRGL. Therefore, when linked to non-nuclear molecules the NLS signal peptide of AGN is able to transport the attached compounds into the nucleus. [Moroianu J, Riordan J F. Identification of the nuclear targeting signal of human angiogenin. Biochem Biophys Res Comm 203:1765-1772, 1994].

CoQ-10 formulation may include optionally one or more bio-active agents, an acceptable carrier, such as oil, or other suspending agent; flavoring, coloring agents or combinations thereof.

Optional bio-active agents that can be incorporated into the CoQ-10 compositions of the present invention include, without limitation, L-carnitine, phospholipids, antioxidants, vitamins, amino acids, proteins, essential minerals and derivatives thereof or combinations thereof.

L-carnitine is recognized in the art, a bio-activity that facilitates transport of materials through the mitochondrial membrane. L-carnitine is an essential co-factor in fatty acid metabolism that helps move fatty acids to the mitochondria from the cytoplasm. This is an important process required for the cellular uptake of CoQ-10. Carnitine is often used for heart conditions and it may be useful to treat angina or chest pain. Carnitine is also useful in the treatment of CHF and intermittent claudication. Although carnitine does not increase blood flow, it is believed that it helps muscles to perform better under difficult painful circumstances, such as those associated with claudication.

In some embodiments of the present invention, L-carnitine is included in combination with CoQ-10. Suitable ratios of L-carnitine and CoQ-10 are known in the art and include those described in U.S. Pat. No. 4,599,232, the teachings of which are incorporated herein in their entirety. The actions of carnitine and CoQ-10 are interrelated. In fact, carnitine, through beta-oxidation of fatty acids, is able to restore the energy supplies necessary for cell life, whereas CoQ-10 is able to restore the ATP supplies necessary for the energetic metabolic processes of the cell.

In the present invention, the effective amounts of L-carnitine in a mixed composition may range from about 0.1% to 75% by weight, preferably about 1% to 50% by weight, and most preferably about 5% to 25% by weight.

Phospholipids are fats that are essential to the healthy structure of cell membranes, particularly, in the brain. Docosahexaenoic acid (DHA) is an essential fatty acid present in brain phospholipids. It works together with the cerebral bio-active molecules to achieve the composition of key phospholipids needed for optimal cell membrane function. Additionally, DHA helps protect against damage that can kill cells and cause the breakdown of the brain's cellular structure.

The formulations of the invention can further include various phospholipids. Non-limiting examples include phosphatidyl glycerol, phosphatidyl inositol, phosphatidyl serine, phosphatidyl choline, phosphatidyl ethanolamine, as well as phosphatidic acids, ceramides, cerebrosides, sphingomyelins and cardiolipins.

In the present invention, the effective amounts of phospholipids in a mixed composition may range from about 0.1% to 75% by weight, preferably about 1% to 50% by weight, and most preferably about 5% to 25% by weight.

The formulations of the invention can further include various bio-active ingredients to help promote the functionality of the CoQ-10, or serve as additional nutrients to an individual's diet. Suitable additives can include vitamins and biologically-acceptable minerals. Non-limiting examples of vitamins include vitamin A, B vitamins, vitamin C, vitamin D, vitamin E, vitamin K and folic acid. Non-limiting examples of minerals include iron, calcium, magnesium, potassium, copper, chromium, zinc, molybdenum, iodine, boron, selenium, manganese, derivatives thereof or combinations thereof. These vitamins and minerals may be from any source or combination of sources, without limitation. Non-limiting exemplary B vitamins include, without limitation, thiamine, niacinamide, pyridoxine, riboflavin, cyanocobalamin, biotin, pantothenic acid or combinations thereof.

In the present invention, the effective amounts of vitamins and/or minerals may be incorporated in the compositions according to their respective 'Percent Daily Values'. Vitamin(s), if present, are present in the composition of the invention in an amount ranging from about 1% to 1000% DV. More particularly, the vitamin(s) is present in an amount ranging from about 10% to 250% DV. Most specifically, the vitamin(s) is present in an amount ranging from about 25% to 100% DV. For example, B vitamins are in usually incorporated in the range of about 50% to 1000% DV, i.e., from about 100% to 1000% DV of B12. Folic acid, for example, is generally incorporated in a range of about 25% to 250% DV, biotin is generally incorporated in a range of about 10% to about 200% DV and B6 is incorporated in a range of about 100% to 500% DV.

Mineral(s), if present, are present in the composition of the invention in an amount ranging from about 1% to about 200% DV. More particularly, the mineral(s) are present in the composition ranging from about 10% to 100% DV.

Suitable carriers include but are not limited to, for example, fatty acids, esters and salts thereof, that can be derived from any source, including, without limitation, natural or synthetic oils, fats, waxes or combinations thereof. Moreover, the fatty acids can be derived, without limitation, from non-hydrogenated oils, partially hydrogenated oils, fully hydrogenated oils or combinations thereof. Non-limiting exemplary sources of fatty acids (their esters and salts) include seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, palm oil, rapeseed oil, palm kernel oil, lupin oil, coconut oil, flaxseed oil, evening primrose oil, jojoba, tallow, beef tallow, butter, chicken fat, lard, dairy butter fat, butter or combinations thereof.

Specific non-limiting exemplary fish or marine oil sources include shellfish oil, tuna oil, mackerel oil, salmon oil, menhaden, anchovy, herring, trout, sardines or combinations thereof. In particular, the source of the fatty acids is fish or marine oil (DHA or EPA), soybean oil or flaxseed oil. Alternatively or in combination with one of the above identified carrier, beeswax can be used as a suitable carrier, as well as suspending agents such as silica (silicon dioxide).

Another optional component of the inventive CoQ-10 blend compositions is lecithin. Lecithin, which is conventionally used as a liposome-forming agent, is a phospholipid made up of polar heads pointing inward and non-polar tails pointing outward. Liposome formation can be used to uptake of the dual hydrophobic-hydrophilic components of the inventive compositions provided herein. Liposomes such as lecithin can, therefore, improve the 'absorption' of CoQ-10 compositions of the invention in gastro-intestinal tract.

If present, the amount of lecithin that is included in a mixed composition of the invention ranges from about 0% to about 98% by weight, preferably about 10% to about 60% by weight, more preferably about 20% to about 50% by weight and most preferably about 30% by weight.

The formulations of the present invention can further include probiotic lactic acid bacteria (LAB) in a viable cell preparation or a non-viable cell preparation in the form of a freeze-dried powder or an emulsion for delivery with CoQ-10 formulations.

The probiotic organisms envisaged in accordance with this invention includes a physiologically effective dosage of at least one LAB strain, typically in the form of a freeze-dried powder or emulsion, selected from a group consisting of but not limited to the strains of bacteria of the genus *Lactobacillus* including *L. acidophilus, L. amylovorus, L. animalis, L. bavaricus, L. brevis, L. bulgaricus, L. casei* spp *casei, L. casei* spp *rhamnosus, L. crispatus, L. delbrueckii* ssp *lactis, L.* eichmanni, L. fermentum, L. helveticus, L. jensenii, L. kefir, L. paracasei, L. pentosus L. plantarum, L. reuteri, L. salivarius, and L. sake; the genus *Leuconostoc* including *Leu. cremoris* and *Leu. lactis*; the genus *Bifidobacterium* including *B. adolescentis, B. animalis, B. bifidum, B. breve, B. infantis, B longum*, and *B. thermophilum*; the genus *Pediococcus* including *Ped. acidilactici* and *Ped. pentosus*; the genus *Peptostreptococcus* including *Pep. assacharolyticus*, and *Pep. productus*; the genus *Propionibacterium* including *Pro. acidipropionici, Pro. freudenreichii, Pro. jensenii*, and *Pro. theonii*; the genus *Streptococcus* including *S. cremoris, S. faecium, S. lactis, S. raffinolactis*, and *S. thermophilus*. The probiotic organisms are collectively known as "lactic acid bacteria"; or "LAB".

The effective dosages of probiotic in a mixed composition range between $10^2$ to $10^{12}$ colony forming units; preferably between $10^5$ to $10^{10}$ colony forming units per serving. Wherein the non-viable counts of probiotic in a mixed composition range between $10^2$ to $10^{12}$ colony forming units; preferably between $10^5$ to $10^{10}$ colony forming units per serving.

Formulations/Compositions with "CoQ-10 Blend"

CoQ-10 blends can be formulated in a variety of dosage forms that include, without limitation, chewable tablets, elixirs, liquids, solutions, suspensions, emulsions, capsules, soft gelatin capsules, hard gelatin capsules, caplets, lozenges, chewable lozenges, suppositories, creams, topicals, ingestibles, injectables, infusions, health bars, confections, animal feeds, cereals, cereal coatings, and combinations thereof. The preparation of the above dosage forms are well known to persons of ordinary skill in the art.

Design of formulations/compositions dependent upon the specific applications of CoQ-10. For systemic administration, CoQ-10 blends can be formulated in aqueous solutions, preferably in physiologically compatible buffers. For trans-mucosal administration, diffusion agents that could cross the mucosal barrier to be used in the formulation. Such agents are generally known in the art.

For oral administration, CoQ-10 blends can be combined with carriers suitable for inclusion into tablets, pills, capsules, liquids, gels, syrups, slurries, and suspensions. In a preferred embodiment, administration is by soft gel capsule. Soft, sealed capsules may be made of gelatin and a plasticizer, such as glycerol or sorbitol. Preferably, the gel material is a bovine gelatin, fish gelatin, lecithin, fatty acid(s), oil or wax. CoQ-10 and other ingredients are dissolved or suspended in suitable liquids, including oils, paraffin oil or liquid polyethylene glycols, optionally in combination with a stabilizer. Preferred oils include seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, palm oil, rapeseed oil, palm kernel oil, lupin oil, coconut oil, flaxseed oil, and evening primrose oil.

For administration by inhalation, CoQ-10 blends are delivered in the form of an aerosol spray with the use of a suitable propellant from pressurized packs or a nebulizer. CoQ-10 blends can also be formulated for parenteral administration, e.g., by bolus injection or continuous infusion. Such formulations can be suspensions, solutions or emulsions in oily or aqueous vehicles, and can contain agents to suspend, stabilize and/or disperse active ingredients. For application to the skin, CoQ-10 blends can be formulated into a suitable gel, magma, cream, ointment, or other carrier. For application to the eyes, the source of CoQ-10 blends can be formulated in aqueous solutions, preferably in physiologically compatible buffers.

Controlled-Release

In addition to the common dosage forms, the CoQ-10 blends of the present invention may also be administered by controlled release mechanism, delivery devices, or both, which are well known to those of ordinary skill in the art, such as those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, the disclosures of which are hereby incorporated by reference. These pharmaceutical compositions can be used to provide slow or controlled-release of CoQ-10 blends using, for example, hydropropylmethyl cellulose in varying proportions to provide the desired release effects, other polymer matrices, gels, permeable membranes, osmotic systems, multi-layer coatings, microparticles, liposomes, microspheres, or the like, or a combination thereof.

The controlled-release of CoQ-10 blends may be stimulated by various inducers, for example pH, temperature, enzymes, water, or other physiological conditions or compounds. The term "controlled-release component" in the context of the present invention is defined herein as a compound or compounds, including polymers, polymer matrices, gels, permeable membranes, liposomes, microspheres, or the like, or a combination thereof, that facilitates the controlled-release of CoQ-10 in a defined formulation.

Advantages of controlled-release formulations may include: i) extended activity of the drug; ii) reduced dosage frequency; and iii) increased patient compliance. Controlled-release formulations of the invention are designed to release an amount of CoQ-10 that provides a desired physiological effect, followed by the gradual and continuous release of other amounts of active ingredients to maintain this level of effect over an extended period of time. In order to maintain this constant level of effect in the body, CoQ-10 needs to be released at a rate that will replenish the amount of CoQ-10 being metabolized and excreted by the body.

Methods of Administering CoQ-10 Formulations/Compositions

Formulations/compositions based on CoQ-10 blend of the present invention and pharmaceutical formats thereof can be used to treat any number of conditions. "Treat" as used herein refer to reduction in severity and/or frequency of symptoms, elimination of symptoms and/or underlying cause, prevention of the occurrence of symptoms and/or their underlying cause, and improvement or remediation of damage that is associated with a particular condition.

The compositions according to the invention can be administered in a circumstance in which increased CoQ-10 levels are desired. Disease states, disorders or conditions which may be treated include but are not limited to cardiovascular conditions including but not limited to coronary heart disease, irregular heartbeat, high blood pressure, and certain blood circulation disorders; age-related degenerative diseases, periodontal disease, impaired memory, fatigue, immune system impairment, and the aging process. The amount of CoQ-10 to be administered depends upon the degree of the effect desired. Those skilled in the art will derive appropriate dosages and schedules of administration to suit the specific circumstances and needs of an individual.

Generally, the formulations as described herein are suitable for administration as a daily dose. The dose may be administered once daily or, if desired, in several, optionally equal, partial doses. Dosage depends upon various factors including sex, age, weight and individual condition. For some individuals, particularly those with specific conditions, higher doses or more frequent doses may be indicated.

EXAMPLES

Compositions containing CoQ-10, LF and AGN can be prepared either by mixing effective amounts of the all three active ingredients into a formula, as individual components; or by adding an effective dosage of a premix of two or all of the three active ingredients at specific pre-calculated ratios.

Example-1

CoQ-10/LF/AGN Premix Compositions

TABLE 1

| | CoQ-10:LF:AGN Premix | | | | |
|---|---|---|---|---|---|
| Ingredient | 10:3:1 Premix | | 20:6:1 Premix | | 10:6:1 Premix |
| CoQ-10 | 100 mg | 60 mg | 100 mg | 60 mg | 100 mg |
| LF | 30 mg | 18 mg | 30 mg | 18 mg | 60 mg |
| AGN | 10 mg | 6 mg | 5 mg | 3 mg | 10 mg |
| Total Premix | 140 mg | 84 mg | 135 mg | 81 mg | 170 mg |

Appropriate CoQ-10/LF/AGN premix can be incorporated into a specific formulation, at effective amounts as required. For instance, adding 250 mg of CoQ-10/LF/AGN premix (10:3:1) to formulations amounts to 178.6 mg of CoQ-10, 53.6 mg of LF, and 17.8 mg of AGN.

Example-2

LF/AGN Premix Compositions

TABLE 2

| | LF:AGN Premix | | | | |
|---|---|---|---|---|---|
| Ingredient | 3:1 Premix | | 2:1 Premix | | 6:1 Premix |
| LF | 30 mg | 18 mg | 30 mg | 150 mg | 60 mg |
| AGN | 10 mg | 6 mg | 15 mg | 75 mg | 10 mg |
| Total Premix | 40 mg | 24 mg | 45 mg | 225 mg | 70 mg |

Appropriate LF/AGN premix can be incorporated into a specific formulation, at effective amounts as required. For instance, adding 250 mg of LF/AGN premix (6:1) to formulations amounts to 214.3 mg of LF, and 35.7 mg of AGN.

Formulations for Cardiovascular Health

Example-3

Soft Gel or Soft Gelatin Capsules for Cardiovascular Health

For cardiovascular health, exemplary soft gel or soft gelatin capsules can be prepared, without limitation, by dispersion of CoQ-10 blend in an appropriate vehicle to form a high viscosity mixture, by using conventional methods well known in the art. Soft elastic gelatin capsules have a soft, globular gelatin shell, somewhat thicker than that of hard gelatin capsules. In such soft gel formats, gelatin is plasticized by the addition of plasticizing agent, e.g., glycerin, sorbitol, or a similar polyol. The hardness of the capsule shell can be altered with appropriate type of gelatin and the amounts of plasticizer and water. Soft gelatin shells may contain a preservative, such as methyl- and propylparabens and sorbic acid, to prevent any fungal growth. CoQ-10 blend may be dissolved or suspended in a liquid vehicle or carrier, such as vegetable or mineral oils, glycols such as polyethylene glycol and propylene glycol, triglycerides, surfactants such as polysorbates, or a combination thereof. Typically, the weight of the capsule may range between about 100 to 2500 milligrams; in particular, weigh between about 500 and 2000 milligrams; and more specifically, weigh between about 750 and 1500 milligrams.

TABLE 3

| Ingredient | Per Serving | % DV |
|---|---|---|
| CoQ-10 | 100 mg | † |
| Lactoferrin* | 30 mg | † |
| Angiogenin* | 10 mg | † |
| Acetyl L-carnitine | 100 mg | † |
| Non-GE Soy Lecithin | 15 mg | † |
| Vitamin-B6 (from Pyridoxine HCl) | 5 mg | 250% |
| Vitamin-E (d-Alpha-Tocopherol Acetate) | 30 IU | 100% |
| Selenium (from Selenium Aspartate) | 69 mcg | 100% |
| Copper (76.7% Copper Oxide) | 2 mg | 100% |
| Flaxseed Oil | 300 mg | † |

*LF and AGN can be incorporated as 40 mg (3:1) premix instead of individual ingredients.

Formulations for Sports Nutrition

The term "sports performance" as used herein, refers to the ability of the athlete's muscles to perform when participating in sports activities, including but not limited to, aerobic exercise, and body building. Enhanced sports performance, strength, speed and endurance are measured by an increase in muscular contraction strength, shortening of muscle reaction time between stimulation and contraction. Sports performance is intended to stimulate muscle tissue through contraction and extension of the muscle fibers. Each contraction and extension, when performed under stress, results in damage to the muscle tissue. The damaged tissue is repaired after the exercise, which leads to formation of additional muscle tissue resulting in muscle growth.

During exercise-related tissue recovery, muscle requires protein (the source of amino acids), calories and other nutrients, including vitamins, salts, minerals and phytochemicals. Previous inventions have utilized specific application of certain amino acids (carnitine, glutamine, isoleucine, leucine, and valine) to exert net stimulatory effects on protein synthesis in skeletal muscle.

The purpose of sports nutrition is to build more muscle tissue faster and to prevent injuries. A variety of products are marketed for this purpose including protein powders, supplemented amino acids, hormones, pro-hormones, and hormone-like chemicals. Protein powders are the most common form of dietary supplements in sports nutrition. Most athletes supplement their daily diet with extra protein in the form of powders or ready-to-drink protein shakes. Protein is metabolized to its building blocks, the amino acids, which can be used by the body to synthesize necessary cellular mass and anabolic hormones for synthesis of new muscle tissue.

Incorporation of CoQ-10 blend of the present invention, with specific ingredients provides several synergistic health benefits, including production of an anabolic (body building) metabolic reaction when the product is consumed.

As used herein, "source of amino acid" means any peptide, polypeptide, protein or any complex of individual amino acids or individual amino acid. Throughout the present specification, as part of the sports performance supplement of the invention, whey protein or a derivative thereof are identified as the preferred source of amino acids or protein. A suitable protein could also be obtained from whey, milk peptides and milk serum, casein and casein hydrolysates, albumin including chicken egg albumin, and soy, may be used as a source of amino acids.

Sports performance supplement compositions may further comprise various vitamins and antioxidants, including vitamin-A (β-carotene), B-complex (including thiamine, niacin, nicotinic acid, niacinamide, pantothenic acid, pyridoxine, cyanocobalamin, biotin and folic acid), vitamin-C (ascorbic acid), vitamin-D, and vitamin-E in amounts equal to or exceeding the recommended minimum daily requirements. Suitable antioxidants include phytophenols (eg. catechols from tea) and bioflavonoids (eg. anthocyanins from grapes).

Suitable salts include, but not limited to, alkali and alkaline earth metal salts, for example sodium, potassium or calcium salts, while suitable minerals include, but not limited to, magnesium, chromium, selenium, or zinc.

The sports performance supplement compositions of the present invention may be provided in a variety of formats, including but not limited to, liquid form, powder form, or protein bar form. Powders are preferable and are prepared to be suitable for mixing with water or other liquids. The sports performance supplement compositions in powder or granular form may be provided in accordance with customary processing techniques, for example as spray dried powders, or the like.

Example-4

Protein Powders for Body Building (Increasing Lean Mass and Strength)

TABLE 4

| Ingredient | Per Serving | % DV |
| --- | --- | --- |
| Coenzyme Q-10 | 120 mg | † |
| Lactoferrin-(tcr)* | 180 mg | † |
| Angiogenin* | 30 mg | † |
| Vitamin B1 (as Thiamine Mono) | 1.5 mg | 100% |
| Vitamin B2 (as Riboflavin) | 1.7 mg | 100% |
| Vitamin B3 (as Niacinamide) | 20 mg | 100% |
| Vitamin B5 (as Calcium Pantothenate) | 10 mg | 100% |
| Vitamin B6 (as Pyridoxine HCl) | 5 mg | 250% |
| Vitamin B12 (as Cyanocobalamin) | 15 mcg | 250% |
| Folic acid | 400 mcg | 100% |
| Biotin | 300 mcg | 100% |
| Vitamin-C (Calcium L-ascorbate) | 120 mg | 200% |
| Vitamin-E (d-Alpha-Tocopherol Acetate) | 30 IU | 100% |
| L-Glutamine | 5.0 g | † |
| Taurine | 1.0 g | † |
| N-acetyl-creatine | 5.0 g | † |
| N-acetyl-cysteine | 0.5 g | † |
| L-Glycine | 3.0 g | † |
| L-Leucine | 1.0 g | † |
| L-Arginine | 100 mg | † |
| Acetyl L-carnitine | 200 mg | † |
| Sodium (as citrate) | 50 mg | † |
| Potassium (as citrate) | 40 mg | 1% |
| Selenium (from Selenium Aspartate) | 69 mcg | 100% |
| Magnesium (Magnesium Oxide) | 8 mg | 2% |
| Copper (76.7% Copper Oxide) | 2 mg | 100% |
| Chromium (19% Chromium Chloride) | 120 mcg | 100% |
| Milk protein Concentrate | As required | † |

*LF and AGN can be incorporated as 210 mg (6:1) premix instead of individual ingredients.

According to one embodiment, the supplement compositions of the present invention are delivered in powder on a per one "scoop" basis. As used herein, one "scoop" is approximately 28 g of supplement.

Example-5

Supplement for Exercise Recovery

The following formulation promotes tissue recovery after exercise while providing energy and preventing oxidation damage. Vascularization improves as body mass increases. This formulation is particularly useful for body builders including weight lifters, professional athletes and dancers, and particularly for increasing muscle mass. This formulation may be prepared as a powder to be added to milk, water, yogurt or other food substance as a nutritional supplement.

TABLE 5

| Ingredient | Per Serving | % DV |
| --- | --- | --- |
| CoQ-10 | 100 mg | † |
| Lactoferrin* | 60 mg | † |
| Angiogenin* | 20 mg | † |
| Non-GE Soy Lecithin | 15 mg | † |
| Vitamin-B6 (from Pyridoxine HCl) | 5 mg | 250% |
| Vitamin-E (d-Alpha-Tocopherol Acetate) | 30 IU | 100% |
| Selenium (from Selenium Aspartate) | 69 mcg | 100% |
| Copper (76.7% Copper Oxide) | 2 mg | 100% |
| Protein powder (milk, egg, whey, or soy) | 10-20 g | † |
| L-taurine | 1 g | † |
| N-acetyl creatine | 5 g | † |
| Dehydroepiandrosterone (DHEA) | 50 mg | † |
| Amino Acid blend (glycine, leucine, arginine, taurine) | 4 g | † |
| Choline | 200 mg | † |
| Inositol hexanicotinate | 25 mg | † |

*LF and AGN can be incorporated as 80 mg (3:1) premix instead of individual ingredients.

Nitric oxide (NO) is essential for muscle contraction and dilation of blood vessels. This cellular function is vital for widening of blood vessels to support an increased blood flow for greater oxygen and nutrient delivery. Body builders, in particular, need such increase in blood flow for maximum oxygen and nutrient delivery. Taurine plays an important role in NO production, and is therefore, a useful supplement to maintain or increase NO production.

DHEA is an androgen (male sex hormone) produced in the adrenal glands, and is one of the main precursors of testosterone. DHEA levels can decline up to 90% with age, therefore, is often used to boost sex hormone levels, and used by athletes to boost testosterone levels. Studies have shown that supplementing 50-100 mg of DHEA per day help increase muscle mass and improve overall health condition.

The formulation can optionally contain human growth hormones (hGF) or hGF precursors and stimulators; testosterone or testosterone precursors (eg. androstenediol) and stimulators (extracts from *Tribulus terristis* or *Avena sativa*).

Example-6

Beverages for Cardio-Aerobic Performance

For cardio-aerobic performance, CoQ-10 blends suitable for use in the present invention include any beverage that forms an amount of food residue in the digestive tract or that forms an amount of residue which does not impede or adversely affect a predetermined activity or the outcome of such activity. Such beverages may include, but are not limited to, drinks containing natural, e.g., fruit or vegetable, and/or artificial ingredients such as iced tea or coffee, coffee, herbal teas, fruit juices, sports-drinks, sodas, soft drinks and the like. Suitable beverages may include blends of various ingredients compounded in dry powder form or effervescent tablets that readily dissolve in a fluid, such as water. Such beverages may also comprise a blend of organic ingredients, such as whole herbs, or may include vitamin or herbal enhanced waters in various flavors.

The CoQ-10 formulation suitable for beverage use in the present invention includes, but is not limited to, any flavored drink comprising sugar, malic acid, aspartame, sodium citrate, natural and artificial flavors/colors and phenylalanine.

TABLE 6

| Ingredient | Per Serving | % DV |
| --- | --- | --- |
| Coenzyme Q-10 | 50 mg | † |
| Lactoferrin-(tcr)* | 30 mg | † |
| Angiogenin* | 5 mg | † |
| Pycnogenol (extract from *Pinus pinaster*) | 45 mg | † |
| L-arginine | 100 mg | † |
| L-lysine | 200 mg | † |
| Vitamin-C (as Calcium L-Ascorbate) | 120 mg | 200% |
| Selenium (from Selenium Aspartate) | 69 mcg | 100% |

*LF and AGN can be incorporated as 35 mg (6:1) premix instead of individual ingredients.

In one alternative embodiment of the present invention, an appropriate serving of a drink may also contain B-complex vitamins and/or minerals such that it provides appropriate nutrition.

Lactoferrin-(tcr) may be prepared as described in U.S. Application No. 2005/0197495, which is incorporated herein by reference. Basically, a 1% (v/v) polysorbate-80 solution, a 0.5% solution of vitamin C (as calcium-L-ascorbate) with 10 mM sodium bicarbonate and 95% (w/v) turmeric root extract (0.1% curcumin) were used in the TCR process as surfactant, antioxidant and polyphenolic tiers, respectively. LF powder was dissolved in 100 mL of polysorbate-80 solution with gentle stirring at room temperature for 2 h. Ten minutes after adding 10 g LF to polysorbate-80 (100 mL) the solution was mixed with calcium-L-ascorbate (0.5 g) and 10 mM sodium bicarbonate and stirred at room temperature for 2 h. Ten minutes later, a polyphenolic phase was included with the addition of 1% curcumin to the solution with continuous stirring at room temperature for 2 h. By this process, the aerobic plate count is markedly reduced by more than 99.9% and the endotoxin activity is greatly diminished almost to undetectable level.

Example-7

Meal Replacement Health Bars to Reduce or Prevent Vascular Plaque

For prevention of vascular plaque formation, CoQ-10 blends suitable for use in the present invention can be designed as "health bars" to approximate a meal-equivalent. Such health bars may include rolled oats and bran mixed with the soy protein to form the common bar "oat-soy" material, to which the ingredients of CoQ-10 formulation will be admixed with appetite-stimulants that may include high-fat and sour taste (eg: oil and vinegar); appetite-depressants that may include low-fat, fiber, and bitter taste (eg: starch, edible gum, and quinine). Alternative or additional ingredients may be carbohydrates derived from other grains, fruits, and vegetables; with proteins derived from nuts, beans, eggs, cheese, meat, fish, and fowl. Soluble and insoluble fiber sources include apples, potatoes, and gum plants. Vitamins, minerals, and other additives.

TABLE 7

| Ingredient | Per Serving | % DV |
| --- | --- | --- |
| Coenzyme Q-10 | 30 mg | † |
| Lactoferrin* | 30 mg | † |
| Angiogenin* | 5 mg | † |
| Pantethine | 50 mg | † |
| Lycopene | 1.0 mg | † |
| Lutein | 0.5 mg | † |
| L-carnitine (fumarate) | 50 mg | † |
| Vitamin-B6 (from Pyridoxine HCl) | 2 mg | 100% |
| Vitamin-C (from Calcium Ascorbate) | 60 mg | 100% |
| Lecithin | 100 mg | † |
| Chitosan | 100 mg | † |
| Red yeast rice | 200 mg | † |

*LF and AGN can be incorporated as 35 mg (6:1) premix instead of individual ingredients.

Health bar can be prepared, without limitation, by mixing CoQ-10 blend with all the ingredients of the formulation with excipients (e.g., binders, fillers, flavors, colors, etc.) to a plastic mass consistency. The mass is then either extended or molded to form "rectangular bar" shapes that are then dried or allowed to solidify to form the final product.

Formulations for Healthy Management of Female Hormone Transitions (HT)

Hormones are vital chemical substances in our body. Women, in particular, undergo three major hormonal transitions (HT) during their life-time, namely: "HT-1", the reproductive (menstruation) phase; "HT-2", the peri-menopause phase; and "HT-3", the post-menopause phase. The four major hormones, i.e. estrogen, progesterone, follicle stimulating hormone and luteinizing hormone, are involved with menstrual cycle and reproduction. In women, estrogen circulates in the bloodstream, binds to estrogen receptors to influence the functions of brain, bone, liver, heart and other tissues. Estrogen controls growth of the uterine lining during the first part of the menstrual cycle, causes changes in the breasts during adolescence and pregnancy, and also regulates various metabolic processes, including bone growth and cholesterol levels.

LF is the body's own "natural regulator" of hormones and an active component of the vaginal secretions and uterine luminal fluid. LF occurs in the uterine epithelia at varying levels and fluctuates with the rise and fall of estrogen during the estrous cycle. LF is associated with estrogen; high levels enhance estrogen activity and low levels suppress it. [Zhang Z, Teng C T. Estrogen receptor-related receptor 1 interacts with coactivator and constitutively activates the estrogen response elements of the human lactoferrin gene. J Biol Chem 275:20837-20846, 2000].

Any depletion, deficiency or dysfunction of LF could put women through painful symptoms and predispose several health risks such as osteoporosis, coronary heart disease, and vaginal infections. Research studies have shown that LF supplementation could provide a natural balance during the hormonal transitions. Incorporation of CoQ-10 and AGN to the LF-based female hormonal transition formulations could provide several synergistic health benefits, including alleviation of many painful symptoms. The following CoQ-10 blends are non-limiting examples for health management of all three phases of female HT.

Example-8

CoQ-10/AGN Containing LF-Based Formula for Female HT-1

The formulation described herein, could be beneficial, particularly for women undergoing HT-1 phase on a daily and monthly basis, during their child-bearing years. Women may encounter a recurrent and cyclical set of physical and behavioral symptoms that occur 7-14 days before the menstrual cycle. The symptoms may be troublesome enough to interfere with several aspects of a regular life, collectively referred to as "premenstrual syndrome (PMS)".

TABLE 8

| Ingredient | Per Serving | % DV |
| --- | --- | --- |
| Lactoferrin* | 90 mg | † |
| CoQ-10 | 30 mg | † |
| Angiogenin* | 10 mg | † |
| Borage Oil (>20% Gamma-Linolenic Acid) | 300 mg | † |
| Evening Primrose oil | 150 mg | † |
| Chaste Tree Extract 4:1 (Vitex agnus-castus) | 20 mg | † |
| Vitamin-B1 (from Thiamine Mono) | 1.5 mg | 100% |
| Vitamin-B2 (from Riboflavin) | 1.7 mg | 100% |
| Vitamin-B3 (from Niacinamide) | 20 mg | 100% |
| Vitamin-B5 (from Calcium D-Pantothenate) | 10 mg | 100% |
| Vitamin-B6 (from Pyridoxine HCl) | 10 mg | 500% |
| Vitamin-B12 (from Cyanocobalamin) | 6 mcg | 100% |
| Folic acid | 200 mcg | 50% |
| Biotin | 150 mcg | 50% |
| Calcium (from Calcium Citrate) | 50 mg | 10% |
| Magnesium (from Magnesium Oxide) | 20 mg | 10% |
| Chromium (19% Chromium Chloride) | 30 mcg | 25% |
| Sodium Bicarbonate USP | 10 mg | † |
| Citric acid | 20 mg | † |

*LF and AGN can be incorporated as 100 mg (9:1) premix instead of individual ingredients.

An effective dosage of the formulations, as exemplified above, can be administered in the form of a soft-gel or a two-piece capsule. A suitable two-piece capsule that can hold liquid without any leakage can be prepared by using proper sealant or by converting the liquid into a form which is either solid or semi-solid at room temperature.

Example-9

CoQ-10/AGN Containing LF Compositions for Female HT-2 (AM-Formula)

The formulation described herein, is beneficial for women undergoing HT-2, a phase in every woman's life with the continued absence of a menstrual cycle, leads to menopause. A woman's body adjusts to the declining estrogen during the HT-2 phase by balancing the progesterone levels. Several physical and emotional changes are associated with fluctuating estrogen levels during the hormonal transition to menopause; a process medically termed as "perimenopause", which typically lasts about 5 years for most women.

The following "AM formula" is intended to relieve daytime symptoms including, mood changes, irritability, difficulty with memory and attention span, vaginal dryness, painful intercourse, dry eye syndrome, urinary leakage, skin and hair changes.

TABLE 9

| Ingredient | Per Serving | % DV |
| --- | --- | --- |
| Lactoferrin* | 45 mg | † |
| CoQ-10 | 30 mg | † |
| Angiogenin* | 5 mg | † |
| Vitamin-B6 (from Pyridoxine HCl) | 4 mg | 200% |
| Vitamin-E (d-alpha-Tocopherol Acetate) | 30 IU | 100% |
| Vitamin-C (from Calcium Ascorbate) | 60 mg | 100% |
| Selenium (from Selenium Aspartate) | 40 mcg | 58% |
| Calcium (from Calcium Ascorbate, Citrate) | 50 mg | 10% |
| Magnesium (from Magnesium Oxide) | 5 mg | 2.5% |
| Potassium (from Potassium Chloride) | 20 mg | 0.5% |
| Soy Protein Isolate | 50 mg | † |
| Black Cohosh | 30 mg | † |
| Red Clover 4:1 Extract | 20 mg | † |
| Soy Lecithin | 15 mg | † |
| Sodium Bicarbonate USP | 10 mg | † |

*LF and AGN can be incorporated as 100 mg (9:1) premix instead of individual ingredients.

Example-10

CoQ-10/AGN Containing LF Compositions for Female HT-2 (PM-Formula)

The "PM formula" described herein, is intended to relieve night-time symptoms including hot flashes, night sweats, and insomnia.

TABLE 10

| Ingredient | Per Serving | % DV |
| --- | --- | --- |
| Lactoferrin* | 45 mg | † |
| CoQ-10 | 30 mg | † |
| Angiogenin* | 5 mg | † |
| Vitamin-B5 (as Calcium D-Pantothenate) | 20 mg | 200% |
| Vitamin-E (as d-alpha-Tocopheryl Acetate) | 30 IU | 100% |
| Vitamin-C (from Calcium Ascorbate) | 60 mg | 100% |
| Selenium (from Selenium Aspartate) | 40 mcg | 58% |
| Calcium (from Calcium Ascorbate, Citrate) | 50 mg | 10% |
| Magnesium (from Magnesium Oxide) | 5 mg | 2.5% |
| Potassium (from Potassium Chloride) | 20 mg | 0.5% |
| Gamma-oryzanol | 20 mg | † |
| L-Theanine | 30 mg | † |
| Valerian root | 50 mg | † |
| Soy Lecithin | 15 mg | † |
| Sodium bicarbonate USP | 10 mg | † |

*LF and AGN can be incorporated as 50 mg (9:1) premix instead of individual ingredients.

An effective amount of the AM and PM formulations, as exemplified above, can be administered in the form of a tablet or a two-piece capsule. Tablets can be prepared with pharmaceutically acceptable excipients including fructose-DC, magnesium stearate, stearic acid, CanTab (tableting dextrose, Penford Food Ingredients, Englewood, Colo.), natural flavor and color (if necessary) were blended with the ingredients from Table 10. Each of the above ingredients was placed, in powdered form, into a commercial blender, mixed and, if necessary, passed through a mesh screen to remove aggregates. After 20 minutes of thorough mixing, the composition is cold pressed in a tablet press set at a appropriate pressure and manufacturing methods commonly practiced in the art of manufacturing dietary supplements.

Example-11

CoQ-10/AGN Containing LF Compositions for Female HT-3

The formulation described herein, is beneficial for women undergoing HT-3, which normally occupies one-third of a woman's life, leads to "post menopause" and the total cessation of menstrual cycles. In time, hot flashes may seem milder or less frequent, emotional swings and energy levels may become more stable, and most of the symptoms of menopause have faded. The HT-3 phase differs from the HT-1 and HT-2 phases in the way that the sex hormones are biosynthesized. In women, sex hormones play a critical role in maintaining healthy bones, heart and blood vessels. The deficiency of sex hormones in post-menopause increases the risk of cardiovascular disease, osteoporosis, dryness of the vaginal walls, changes in the urinary tract and weight gain.

TABLE 11

| Ingredient | Per Serving | % DV |
|---|---|---|
| Lactoferrin* | 90 mg | † |
| CoQ-10 | 30 mg | † |
| Angiogenin* | 10 mg | † |
| Flaxseed Oil (>20% alpha-Linolenic Acid) | 300 mg | † |
| Vitamin-D | 200 IU | 50% |
| S-Adenosylmethione (SAM-e) | 200 mg | † |
| Calcium (from Citrate) | 50 mg | 10% |
| Magnesium (from Oxide) | 20 mg | 5% |
| Chromium (19% chromium chloride) | 30 mcg | 25% |
| Sodium Bicarbonate USP | 10 mg | † |
| Citric acid | 20 mg | † |

*LF and AGN can be incorporated as 100 mg (9:1) premix instead of individual ingredients.

An effective dosage of the formulations, as exemplified above in Table 11, can be administered in the form of a soft-gel or a two-piece capsule. A suitable two-piece capsule that can hold liquid without any leakage can be prepared by using proper sealant or by converting the liquid into a form which is either solid or semi-solid at room temperature.

Formulations for Management of Vaginal Health

Example 12

The preparation of vaginal suppository compositions includes well known techniques of rolling (hand shaping), molding (fusion) and cold compression. Suppositories are usually globular or oviform and weigh about 5 grams. Reference is made to Remington's Pharmaceutical Sciences, 18th Edition, Chapter 87, pages 1609-13 (1990), the disclosure of which is expressly incorporated herein by reference.

Preparation of a vaginal suppository containing the CoQ-10 blend can be prepared in accordance with well known techniques in the art. In a typical suppository formulation, the active agents are combined with an appropriate pharmaceutically acceptable suppository base such as cocoa butter, esterified fatty acids, glycerinated gelatin, and various water-soluble or dispersible bases like polyethylene glycols and polyoxyethylene sorbitan fatty acid esters. Various additives, enhancers, or surfactants may be incorporated. Such suppositories will generally be constructed of a mixture of substances that are solid at room temperature but melt at body temperature. The substances commonly used to create such vehicles include, but are not limited to, *theobroma* oil, glycerinated gelatin, hydrogenated vegetable oils, mixtures of polyethylene glycols of various molecular weighty and fatty acid esters of polyethylene glycol.

The vaginal suppository may include a water soluble base to lower surface tension for rapid dispersion of actives. A water-soluble base also decreases the risk of secondary infection. Exemplary water soluble bases include, but are not limited to, corn starch, aloe and cocoa butter.

The vaginal suppository compositions of the present invention may also include propylene glycol, which acts as a surfactant to assist in penetration, contact, and absorption of the active ingredients. Propylene glycol also serves as a preservative and an antimicrobial agent.

Compositions of the vaginal suppository of the present invention may also include a non-ionic surfactant such as polysorbate to promote better surface contact of the ingredients with the vaginal mucosa by further reducing the surface tension.

Compositions of the vaginal suppository of the present invention may also be formulated in combination with other drugs, such as spermicides, antibiotics (antibacterials, antifungals such as fluconazole, antivirals and antiparasitics) and anti-inflammatory agents, thereby further broadening the composition's medical applications.

Compositions of the vaginal suppository of the present invention may also be pH balanced by the addition of a base including, but not limited to, triethanolamine, sodium hydroxide and sodium bicarbonate to adjust the pH to a level compatible with the tissue being treated. In the normal vagina, the pH is in range of about 3.8 to 4.4. A humectant may also be included in the composition of the present invention, such as glycerin, to soothe the area being treated, for example, as a cleansing solution.

Compositions of the present invention may contain a topical anesthetic including, but not limited to, lidocaine hydrochloride and topical steroids, including but not limited to, corticosteroids, to provide relief from pain or itching during the treatment.

As will be understood by those skilled in the art, the regimen for treating vaginal infection will depend on the severity of the infection and the form of the composition. By way of a non-limiting example, where the composition is in the form of a cream, the cream is topically applied to the affected area. Where the composition is in the form of a suppository, it is inserted into the vagina, in a non-limiting example, once or twice daily for 7 days.

Terms used herein are to be given their usual meaning in the art unless otherwise stated. The term "vaginal infection" means any vaginal infection of, bacterial, fungal or parasitic origin. Examples of some of the microorganisms which cause such infections include, but are not limited to, microorganisms of the genus *Candida*, particularly *C. albicans, C. tropicalis* and *C. glabrata, Gardneralla vaginalis*, various mixed anaerobic bacteria and *Peptostreptococcus* bacteria.

One vaginal suppository composition including CoQ-10 blend was formulated as described below. In a non-limiting exemplary embodiment of the present invention, the CoQ-10/LF/AGN (2:10:1) premix formulation (150 mg) can be combined with hydrogen peroxide-producing *Lactobacillus* crispatus (109 CFU/dose) together with an active lactoperoxidase system comprised of either Mixture (A) containing lactoperoxidase (1000 IU), urate oxidase (5000 IU), urate (500 mg) and potassium thiocyante (5 mg); or Mixture (B) containing lactoperoxidase (2000 IU), sodium thiocyanate (10 mg) and benzylalkonium chloride (10 µg). Finally, DMSO (0.1% final concentration) was incorporated to promote rapid tissue penetration.

Treatment of the vaginal infection may vary depending on the severity of the infection and appropriate treatment regimen known to those medical practitioners, particularly gynecologists. An exemplary, non-limiting treatment regimen may involve insertion of a CoQ-10/LF/AGN (2:10:1 premix)-containing suppository into the vagina twice daily for 7 days.

Douche solutions containing CoQ-10/LF/AGN (2:10:1 premix) can be prepared with other optional ingredients including, but not limited to, antimicrobial agents, anaesthetics or antipruitics (such as phenol or menthol), astringents, surface active agents, propylene glycol, glycerin USP and Polysorbate 20 (Liposorb L20). The solution may be initially formed as a concentrated liquid, dissolvable powder or tablet. When use is desired, water may be added, preferably warm in temperature to produce a solution of desired concentration.

Formulations for Bone Health

LF is vital for bone growth and repair; boosts growth and activity of osteoblasts (cells responsible for building bone); reduces, up to 50-70%, the rate at which these cells die, and decreases the formation of osteoclasts (cells responsible for breaking down bone), thereby helps to prevent or reverse osteoporosis. LF could also increase the multiplication of chondrocytes, the cells that build cartilage. Biosynthesized in the bone marrow, LF can modulate inflammatory responses by scavenging toxic "free" iron. This mechanism is important at the sites of inflammation, such as in the rheumatoid joint. LF can bind "free" iron in the synovial fluid and reduce joint inflammation during arthritis. Orally administered LF has preventive and therapeutic effects in the treatment of rheumatoid arthritis. [Cornish J, et al. Lactoferrin is a potent regulator of bone cell activity and increases bone formation in vitro. Endocrinol 145:4366-4374, 2004].

The combination of CoQ-10 blend with LF-based bone health formulations provides several benefits including energy for angiogenesis during formation of bone mass.

Example-13

CoQ-10/AGN Containing LF-Based Bone Health Formulations

TABLE 12

| Ingredient | Actives | % DV |
|---|---|---|
| CoQ-10 | 30 mg | † |
| Lactoferrin (90%)* | 90 mg | † |
| Angiogenin* | 10 mg | † |
| Vitamin-D3 (as Cholecalciferol) | 200 IU | 50% |
| Folic acid | 100 mcg | 25% |
| Chondroitin Sulfate (from Chondroitin Sulfate Sodium) | 25 mg | † |
| Glucosamine Sulfate (from Glucosamine Sulfate Potassium) | 75 mg | † |
| Methylsulfonylmethane (MSM) | 50 mg | † |
| Turmeric root extract | 25 mg | † |
| Calcium (from Calcium Citrate) | 50 mg | 5% |
| Sodium bicarbonate USP | 30 mg | † |
| *Yucca Schidegera* Root Extract | 10 mg | † |

*LF and AGN can be incorporated as 100 mg (9:1) premix instead of individual ingredients.

Other optional active ingredients suitable for the above bone health formulations include but not limited to, S-adenosylmethionine (SAM-e), cerasomal-cis-9-cetylmyristoleate (CMO), and dimethylglycine (DMG).

Formulations for Oral Health-Care

Example-14

CoQ-10 Containing Mouthwash Formulations

A mouthwash base can be prepared by combining cetylpyridinium chloride (1 g), citric acid USP (1 g) and sweetener (q.s), dissolving in 100 mL deionized water and mixing with 100 mL alcohol USP. Flavor oils (peppermint, eucalyptus and clove oils; 1.5 mL) were mixed with polyoxyethylene, and sorbitan monostearate; this blend was slowly added to the hydroalcoholic solution while stirring. A 70% sorbitol solution (200 g) was added and the volume made up to 1000 mL with deionized water. In one embodiment of the present invention, the CoQ-10/LF/AGN (2:10:1 premix) formulation and mouthwash base were mixed to homogeneity at 1:10 ratios. A formulation for a tooth powder is shown in Table 13.

TABLE 13

| Ingredient | % w/w range | % DV |
|---|---|---|
| CoQ-10 | 0.1-5.0% | † |
| Lactoferrin-(tcr)* | 0.1-5.0% | † |
| Angiogenin* | 0.01-1.0% | † |
| Dextrose/Fructose (or polydextrose) | 10.0-90.0% | † |
| xylitol | 0.1-10.0% | † |
| Potassium sorbate | 0.01-1.0% | † |
| Sodium benzoate | 0.01-1.0% | † |
| Zinc gluconate | 0.001-0.1% | † |

*LF and AGN can be incorporated as (6:1) premix instead of individual ingredients.

Formulations for Wound-Care and Skin-Care

CoQ-10 formulations suitable for topical use on the skin can be in the form of an ointment, cream, lotion, paste, oil or spray. Carriers suitable for such use include petrolatum, lanolin, polyethylene glycols (PEG), alcohols and combinations of these substances. Typically, the "active ingredient" in such products is in a concentration of about 0.1% to 15% by weight of the composition, for example from about 0.5% to 2%. The methods for preparing such topically applied formulations are well known in the art.

CoQ-10 formulations suitable for trans-dermal administration can be in the form of single plasters which are suitable for long-term close contact with the skin. Such plasters contains an effective quantity of active ingredients mixed in aqueous buffered solutions that readily dissolve and/or disperse in an adhesive polymer. A suitable concentration of CoQ-10 blend is about 1% to 35%, preferably about 3% to 15%. The methods for making trans-dermal patches are well known in the art. The term "effective amount" refers to a dosage efficient to treat a particular infection and is determined by a person of skill in the art, such as a medical practitioner.

The term skin condition can refer to any state that results from bacterial, parasitic, fungal, insecticidal and actinomycotic infection; which also includes keratinization disorders. Non-limiting examples of microorganisms which can cause such infections include Candidia albicans, microorganisms of the genera *Trichophyton, Epidermophyton* and *Microsporum*, parasites such as *Sarcoptes scabieii, Streptotrichosis*, various dermatophytes, various types of ectoparasites and insects, for example, fleas, lice and mites.

Example-15

Wound Care Formulation

A wound-care formula based on the CoQ-10/LF/AGN (2:20:1 premix) blend can be applied repeatedly from the time when wound first occurs. Preferably, the CoQ-10 formula can be applied about every time when the wound dressing is changed. The CoQ-10 formula can also be applied about every other day; more preferably, every day.

Numerous administration vehicles and delivery methods will be apparent to those of ordinary skill in the art including, without limitation, slow-release systems, liposomal delivery and polymeric matrices. Preparation of each type of CoQ-10 formulation would be within the knowledge of the person of skill in the art, although reference is made to Remington's Pharmaceutical Sciences, 18th Edition (1990), the disclosure of which is expressly incorporated herein by reference.

In a non-limiting example of a skin- or wound-care formulation, a medicated ointment base can be prepared with ingredients (% w/v) as follows: Base (A) contains mineral oil USP (25%), microcrystalline wax (10%), cetyl alcohol (5%), mixed lanolin alcohols (10%), sorbitan sesquioleate, (3%) and propyl p-(OH)-benzoate (0.1%). Base (B) contains glycerine (3%), methyl p-(OH)-benzoate (0.1%) and deionized water (43.8%). Bases (A) and (B) are heated separately to 75° C. and mixed with gentle stirring while cooling to 45° C. to prepare the ointment base. In a non-limiting exemplary embodiment of the present invention, the CoQ-10/LF/AGN (2:20:1 premix) blend and the ointment base can be mixed to homogeneity at 1:5 ratios.

Example-16

Skin Cleansing Formulation

In another non-limiting example of a skin- or wound-care formulation, a skin cleansing solution composition can be prepared. Formula for the base solution is as follows, in which the values are given as % w/w of the total composition: water (81%), propylene glycol (5%), glycerin USP (5%), and polysorbate-20 (5%). The CoQ-10/LF/AGN (2:20:1 premix) blend can be mixed slowly until completely dissolved until solution turns uniform and clear. The solution may be further diluted by adding water. The skin cleansing solution with CoQ-10 blend can be applied to the infected skin site by any suitable means such as cotton wool, cotton swab or the like.

In yet another non-limiting example of a skin- or wound-care formulation, a mild non-irritating skin crème base can be prepared as follows: Oil phase (A) consists of cetearly alcohol (5%), silicone oil 200 fluid (1%), isopropyl myristate (2%) and sodium stearoyl-2-lactylate (2%). Aqueous phase (B) consists of propylene glycol (5%), sodium citrate (0.2%) and purified water to make up to 100% w/v. The components of oil phase (A) are mixed at 65° C., and the components of aqueous phase (B) are mixed at 70° C. Aqueous phase (B) is added to oil phase (A) under cooling with moderate agitation. In an exemplary embodiment of the present invention, the CoQ-10/LF/AGN (2:20:1 premix) blend and the ointment base can be mixed to homogeneity at a 1:10 ratio.

In yet another non-limiting example of a skin- or wound-care formulation, a makeup crème base can be prepared as following: Mixture (A) contains magnesium aluminum silicate (2.6%), sodium carboxy-methyl cellulose (0.4%) and deionized water (42.4%). Mixture (B) contains a dispersing agent (0.3%), propylene glycol (5.0%) and deionized water (12.3%). Mixture (C) contains talc (18.5%), kaolin (1.3%), titanium dioxide (3.7%) and iron oxides, (1.5%). Mixture (D) contained isopropyl myristate (5.0%), strearyl alcohol (2.0%), lanolin absorption base (2.0%), sorbitan monolaurate (0.75%), polyoxyethylene (20) sorbitan monolaurate (2.25%) and perfume. Solids of (A) are blended, added to water at 80° C. and stirred until smooth. Contents of (C) are pulverized and added to (B) and passed through a colloid mill to yield a smooth paste. Mixture of (B)+(C) is added to (A) and heated to 60-65° C. The contents of (D) are then heated to 70° C. and mixed with the (A)+(B)+(C) blend; stirred until the temperature reached 45° C., perfume is added and mixed until cool. In an exemplary embodiment of the present invention, the CoQ-10/LF/AGN (2:20:1 premix) blend and the makeup crème base can be mixed to homogeneity at a 1:10 ratio.

In yet another non-limiting example of a skin- or wound-care formulation, an antiperspirant base can be prepared as follows: Oil phase (A) is prepared with mineral oil (23%), calcium stearoyl-2-lactylate (3.2%) and PEG 400 dioleate, (0.8%). Aqueous phase (B) contains glycerine (3%), 60% sodium lactate (10%) and purified water (20%). Mixture (C) contains 50% aluminum chlorohydrate (40%). Mixtures (A), (B) and (C) are separately heated at 70° C. Aqueous phase solution (B) is quickly added to (C) followed by mixing of (A) with moderate agitation while cooling. In an exemplary embodiment of the present invention, the CoQ-10/LF/AGN (2:20:1 premix) blend and the antiperspirant base can be mixed to homogeneity at a 1:10 ratio.

Example-17

Prophylactic Migraine Formulation

CoQ-10 has been shown to be effective to reduce the number and severity of migraine headaches in migraneurs when taken as a daily supplement. The following formulation combines CoQ-10 with other components known to reduce the number and severity of migraines, such as riboflavin, and magnesium in a formulation that may be taken daily. The addition of angiogenin promotes vascular health which is beneficial for prevention of vascular type headaches such as migraine. The formulation may optionally include feverfew at 20-80 mg/day, preferably about 50 mg/day.

TABLE 14

| Ingredient | Per Serving | % DV |
|---|---|---|
| Lactoferrin* | 90 mg | † |
| CoQ-10 | 30 mg | † |
| Angiogenin* | 30 mg | † |
| Calcium (from Citrate) | 50 mg | 10% |
| Magnesium (from Oxide) | 400 mg | 100% |
| Riboflavin | 10 mg | 500% |
| Sodium Bicarbonate USP | 10 mg | † |
| Citric acid | 20 mg | † |
| Tyrosine | 50 mg | † |

*LF and AGN can be incorporated as 120 mg (3:1) premix instead of individual ingredients.

A pharmaceutical composition of CoQ-10 blend can be prepared with the ingredients listed in Table 14. Appropriate ratios of CoQ-10/LF/AGN and the remaining actives were mixed to homogeneity and the composition is encapsulated in hydroxypropylmethyl cellulose (HPMC) two-piece capsules according to methods commonly practiced in the art of manufacturing of dietary supplements.

Formulations for Uro-Genital Health

The present invention also describes compositions and methods for maintaining uro-genital health, improving sexual function, improving energy, enhancing feelings of well-being and increasing muscle mass, by administering CoQ-10/LF/ANG mixtures, in combination with other natural and organic constituents.

Example-18

Formula for Male Virility and Enhancing Sexual Performance

The below-described composition with CoQ-10 blend, when administered can optimize the inflow of sufficient blood to promote smooth muscle relaxation. The effect is sufficient in the corpus cavernosum to sustain smooth muscle relaxation and thereby raise energy levels, improve sexual function, enhance feelings of well-being and increase muscle mass in the human male. Additional active ingredients can be added to achieve incidental benefits. For instance, saw palmetto is especially helpful for overcoming glandular weakness and to regenerate sexual glands. It is a well-known dietary aid for increasing male prostate health.

TABLE 15

| Ingredient | Per Serving | % DV |
|---|---|---|
| Coenzyme Q-10 | 30 mg | † |
| Lactoferrin-(tcr)* | 90 mg | † |
| Angiogenin* | 30 mg | † |
| Vitamin-B6 (a Pyridoxine HCl) | 4 mg | 200% |
| Vitamin-C (Ca-ascorbate) | 60 mg | 200% |
| Vitamin-E (acetate) | 60 IU | 200% |
| Zinc (32% zinc citrate) | 7.5 mg | 50% |
| Lecithin (granules) | 30 mg | † |
| Damiana extract | 25 mg | † |
| Sarsaparilla extract | 25 mg | † |
| Saw Palmetto Std Extract (85% Fat) | 25 mg | † |
| L-Theanine (decaffeinated)* | 25 mg | † |
| Acetyl-L-carnitine | 100 mg | † |
| L-Arginine HCl (81.6% ARG) | 50 mg | † |
| L-Tyrosine | 50 mg | † |
| Sodium bicarbonate | 7.5 mg | † |

*LF and AGN can be incorporated as 120 mg (3:1) premix instead of individual ingredients.

The above ingredients can be used to prepare capsules, or tablets. Lactose and corn starch are commonly used as diluents for capsules and as carriers for tablets. Lubricating agents, such as magnesium stearate, are typically added to form tablets. Additional inert ingredients may be added as desired to achieve a desired taste, color or consistency.

Example-19

Formula for Female Libido and Enhancing Sexual Performance

Proper sexual functioning in women depends on the sexual response cycle, which consists of an anticipatory mental set (sexual motive state or state of desire), effective vaso-congestive arousal (swelling and lubrication), orgasm, and resolution. In women, orgasm is accompanied by contractions of the muscles of the outer third of the vagina. Orgasm is followed by resolution, a sense of general pleasure, well-being, and muscular relaxation. During this phase, women may be able to respond to additional stimulation almost immediately. To increase blood flow in the female genital tissue is also useful to improve sexual wellness. The following CoQ-10 blend provides a safe, natural way to preserve and maintain sexual responsiveness, endurance and enjoyment.

TABLE 16

| Ingredient | Per Serving | % DV |
|---|---|---|
| Coenzyme Q-10 | 30 mg | † |
| Lactoferrin-(tcr)* | 90 mg | † |
| Angiogenin* | 30 mg | † |
| Lysozyme | 10 mg | † |
| Cranberry Extract | 25 mg | † |
| L-Theanine (decaffeinated) | 50 mg | † |
| *Echinacea Purp.* Root Extract 4:1 | 25 mg | † |
| Acetyl-L-carnitine | 100 mg | † |
| Tyrosine | 50 mg | † |
| Magnesium (as oxide) | 4 mg | 1% |
| Potassium Phosphate (98% di-basic) | 5 mg | † |
| Sodium bicarbonate | 10 mg | † |

*LF and AGN can be incorporated as 120 mg (3:1) premix instead of individual ingredients.

The above ingredients can be used to prepare capsules, or tablets. Lactose and corn starch are commonly used as diluents for capsules and as carriers for tablets. Lubricating agents, such as magnesium stearate, are typically added to form tablets. Additional inert ingredients may be added as desired to achieve a desired taste, color or consistency.

Formulations for Brain Health & Stress Management

The present invention, CoQ-10 blend, in combination with organic nutrients is aimed at stimulating the brain to produce a positive psychoactive effect for stress management. CoQ-10 blend, a powerful biological delivery medium, could enhance the bio-availability of essential nutrients to the brain, to effectively maintain the mental fitness.

In addition to CoQ-10, LF and AGN, the supplementary constituents include phosphatidyl serine, phenylalanine, B-complex vitamins, vitamin C, vitamin E, taurine, choline, copper, chromium and bicarbonate. These constituents are incorporated in an effervescent drink formulation as follows:

Example-20

Effervescent Drink Mix (Powder Blend) for Brain Health & Stress Management

TABLE 17

| Ingredient | Per Serving | % DV |
|---|---|---|
| Coenzyme Q-10 | 60 mg | † |
| Lactoferrin-(tcr)* | 90 mg | † |
| Angiogenin* | 30 mg | † |
| Vitamin B1 (as Thiamine Mono) | 1.5 mg | 100% |
| Vitamin B2 (as Riboflavin) | 3.4 mg | 200% |
| Vitamin B3 (as Niacinamide) | 20 mg | 100% |
| Vitamin B5 (as Calcium Pantothenate) | 25 mg | 250% |
| Vitamin B6 (as Pyridoxine HCl) | 10 mg | 500% |
| Vitamin B12 (as Cyanocobalamin) | 15 mcg | 250% |
| Folic acid | 200 mcg | 50% |
| Vitamin-C (Calcium L-ascorbate) | 120 mg | 200% |
| Vitamin-E (d-Alpha-Tocopherol Acetate) | 60 IU | 200% |
| Phosphatidyl serine | 100 mg | † |
| Phenylalanine | 500 mg | † |
| Taurine | 400 mg | † |
| Choline (as Dihydrogen citrate) | 300 mg | † |
| Malic acid | 200 mg | † |
| L-Glycine | 150 mg | † |
| L-theanine (decaffeinated) | 25 mg | † |
| Aspartic acid | 5.0 mg | † |
| Zinc (as Zinc Gluconate) | 3.0 mg | † |
| Copper (76.7% Copper Oxide) | 0.5 mg | 25% |
| Chromium (19% Chromium Chloride) | 60 mcg | 50% |

*LF and AGN can be incorporated as 120 mg (3:1) premix instead of individual ingredients.

Pharmaceutically acceptable excipients also contained in the above nutritional drink composition include, but are not limited to, bicarbonate/citric acid mixture, fructose-DC, magnesium stearate, stearic acid with natural cherry flavor and natural red color and all the ingredients were blended to a homogenous mixture. Other inert ingredients may be added as required to achieve a desired taste, color or consistency. For optimum results, the serving of the present invention should be taken at least an hour before the meal.

The primary active constituents have the following advantages: Phosphatidyl serine (PS), a phospholipid commonly found in both plant and animal foods, is a naturally derived brain nutrient. Oral supplementation with PS benefits cognitive functions, particularly in adults in their mature years. The U.S. Food and Drug Administration (FDA) authorized two health claims for PS, the first claim "phosphatidyl serine may reduce the risk of cognitive dysfunction in the elderly", and the second claim, "phosphatidyl serine may reduce the risk of dementia in the elderly".

The essential amino acid phenylalanine contained in the formulation is converted by the brain into neurotransmitters (noradrenaline and dopamine) and neuromodulator (β-phenylethylamine) with the help of cofactors folic acid, vitamin C, vitamin B-6 and copper. Taurine, the sulfur-containing amino acid in the formulation, is another neuromodulator that is important for the regulation of electrically active tissues (eg. brain and heart). Taurine also helps to promote a mellow mood without sedation or tranquilization. Theanine, the polyphenolic extract from green tea in the formulation, is a powerful natural antioxidant and a free radical scavenger. When this green tea free radical scavenging antioxidant enters the brain, a feeling of well-being results, which is a positive reinforcement of brain activity.

Finally, the induction of carbon-dioxide bubbles through the bicarbonate effervescence could directly reach the brain. The $CO_2$ released in the mouth could instantly diffuse into the nasopharyngeal tissue and rapidly cross the blood-brain barrier. This results the following two effects: i) the $CO_2$ causes vasodilation (increase in blood flow to and within the brain), and ii) the $CO_2$ also increases the permeability of the blood-brain barrier, thereby transporting more nutrients. These effects could make the onset of the psychoactive outcome more rapid and intense.

Formulations for Detoxification and Internal Cleansing

Human body encounters toxins from both internal and external sources on a regular basis. Fortunately, physiological systems such as the liver, kidneys, lungs, intestines, and blood work continuously to clean out every cell, organ and tissue.

The colon is one of the primary organs involved in the body's detoxification process. Harmful substances such as bacteria, pesticides, food additives, environmental pollutants, drugs and chemicals are filtered out by an internal detoxification process and eliminated through the intestinal tract.

Example-21

Formula for Colon Cleansing

The body's first line of defense is a healthy colon. However, this intestinal detoxification process can breakdown from: overexposure to environmental pollutants, food and water, poor diet, lack of adequate fiber, excessive alcohol and caffeine, high stress, lack of exercise, overuse of antibiotics and prescription medications. When the body's internal detoxification process breaks down, toxins circulate into the bloodstream instead of being eliminated through the colon, cause illness, digestive ailments and other serious health disorders. This produces a state of toxicity and colon cleansing becomes one of the most important steps in detoxification.

TABLE 18

| Ingredients | Per Serving | % DV |
|---|---|---|
| Lactoferrin* | 90 mg | † |
| Angiogenin* | 30 mg | † |
| Coenzyme Q10 | 30 mg | † |
| Vitamin-C | 60 mg | 100% |
| Probiotic lactic acid bacteria | 250 mg | † |
| Cascara Sagrada | 125 mg | † |
| Peppermint (oil) | 125 mg | † |
| Gingerol (oil) | 125 mg | † |
| Fennel (oil) | 125 mg | † |
| Chlorella | 250 mg | † |

*LF and AGN can be incorporated as 120 mg (3:1) premix instead of individual ingredients.

An effective dosage of the formulations, as exemplified above, can be administered in the form of a soft-gel or a two-piece capsule. A suitable two-piece capsule that can hold liquid without any leakage can be prepared by using proper sealant or by converting the liquid into a form which is either solid or semi-solid at room temperature. Embodiments of the invention are also directed to the use of the above formulation in an enema.

Besides the multifunctional health benefits of CoQ-10/LF/AGN blend, the primary active constituents have the following advantages: *Chlorella* contains over 19 amino acids, beta-carotene, potassium and other valuable vitamins and minerals, and enzymes. It is a potent detoxifier, cell enhancer, and blood cleanser. *Chlorella* liquid extract is a powerful internal deodorant that reduces odors originating in the digestive tract. Peppermint cleans and strengthens the entire body, especially the bowels. Fennel seed is used for colic, gas and intestinal problems. It helps stabilize the nervous system, improves digestion, and has a diuretic effect. Cascara Sagrada promotes peristaltic action (bowel movement) in the intestinal tract.

Probiotic lactic acid bacteria (LAB) are vital for a healthy bowel. These friendly bacteria synthesize nutrients in the intestinal tract, counteract harmful bacteria that disturb proper digestion and elimination as described in Naidu U.S. Pat. No. 6,797,266 B2, issued Sep. 28, 2004.

Probiotic LAB useful in embodiments of the present invention include physiologically effective dosages of at least one LAB strain, typically in the form of a freeze-dried powder, emulsion or viable or non-viable cell preparation, selected from a group consisting of, but not limited to, strains of bacteria of the genus *Lactobacillus* including *L. acidophilus, L. amylovorus, L. animalis, L. bavaricus, L. brevis, L. bulgaricus, L. casei* spp. *casei, L. casei* spp. *rhamnosus, L. crispatus, L. delbrueckii* ssp. *lactis, L. eichmanni, L. fermentum, L. helveticus, L. jensenii, L. kefir, L. paracasei, L. pentosus, L. plantarum, L. reuteri, L. salivarius* and *L. sake*; strains of bacteria of the genus *Leuconostoc* including *Leu. cremoris* and *Leu. lactis*; strains of bacteria of the genus *Bifidobacterium* including *B. adolescentis, B. animalis, B. bifidum, B. breve, B. infantis, B. longum*, and *B. thermophilum*; strains of bacteria of the genus *Pediococcus* including *Ped. acidilactici* and *Ped. pentosus*; strains of bacteria of the genus *Peptostreptococcus* including *Pep. assacharolyticus* and *Pep. productus*; strains of bacteria of the genus *Propionibacterium* including *Pro. acidipropionici, Pro. freudenreichii, Pro. jensenii* and *Pro. theonii*; strains of bacteria of the genus *Streptococcus* including *Strep. cremoris, Strep. faecium, Strep. lactis, Strep. raffinolactis* and *Strep. thermophilus*.

Dosages of probiotic bacteria contained in the compositions of the present invention comprise bacterial counts in the range of $10^2$ to $10^{12}$ colony forming units (for viable LAB) or microbial cells (for non-viable LAB). Optimal dosages of probiotic bacteria contained in the compositions of the present invention comprise bacteria counts in the range of $10^5$ to $10^{10}$ colony forming units (for viable LAB) or microbial cells (for non-viable LAB). Colony forming units are defined as total number of viable bacteria grown on agar medium.

Example-22

Formula for Liver Cleansing

TABLE 19

| Ingredients | Per Serving | % DV |
|---|---|---|
| Lactoferrin* | 90 mg | † |
| Angiogenin* | 30 mg | † |
| Coenzyme Q10 | 30 mg | † |
| Vitamin C | 60 mg | 100% |
| Vitamin E | 30 IU | 100% |
| Lecithin | 30 mg | † |
| Cysteine peption | 500 mg | † |
| Milk Thistle | 250 mg | † |
| Dandelion extract (1:1 in ethanol) | 10 mg | † |

*LF and AGN can be incorporated as 120 mg (3:1) premix instead of individual ingredients.

Besides the multifunctional health benefits of CoQ-10/LF/AGN blend, the primary active constituents have the following advantages: Milk Thistle inhibits the enzyme, lipoxygenase, thereby prevents the formation of leukotrienes that are responsible for inflammations. It also prevents free radical damage to liver cells and stimulates the production of new liver cells. Milk Thistle helps protect normal liver function from damage by alcohol, environmental stress, and other toxic substances. Another potent liver detoxificant is dandelion. It stimulates the liver to detoxify poisons, promotes healthy circulation, and strengthens weak arteries. Dandelion (*Taraxacum officinale*) above ground parts (1:1 in 25% alcohol) is a promoter of healthy circulation, skin toner, and blood vessel cleanser.

Example-23

Formula for Blood Cleansing

TABLE 20

| Ingredients | Per Serving | % DV |
|---|---|---|
| Lactoferrin* | 90 mg | † |
| Angiogenin* | 30 mg | † |
| Coenzyme Q10 | 30 mg | † |
| Vitamin-C | 60 mg | 100% |
| Turmeric root extract | 30 mg | † |
| Burdock root extract | 250 mg | † |
| Rosemary leaf extract | 250 mg | † |
| Red Clover extract | 50 mg | † |
| Yarrow (1:1 ethanol extract) | 10 mg | † |

*LF and AGN can be incorporated as 120 mg (3:1) premix instead of individual ingredients.

All ingredients from Table 20 can be compressed into a tablet form. Pharmaceutically acceptable excipients including fructose-DC, magnesium stearate, stearic acid, CanTab (tableting dextrose, Penford Food Ingredients, Englewood, Colo.), natural cherry flavor and natural blue color were blended with the ingredients from Table 20. Each of the above ingredients was placed, in powdered form, into a commercial blender, mixed and, if necessary, passed through a mesh screen to remove aggregates. After 20 minutes of thorough mixing, the composition is cold pressed in a tablet press set at a maximum pressure of 6.4 tons yielding chewable tablets.

The primary active constituents have the following advantages: Burdock root extract is one of the best blood purifiers. It also reduces swelling around joints, dissolves calcification deposits, and clears blood of harmful acids. Red Clover is also a very strong blood purifier. It is used as a tonic for the nerves and as a sedative for nervous exhaustion. Yarrow acts as a blood cleanser, opens the pores to permit free perspiration for elimination of waste, relieving the kidneys. It also helps to regulate the function of the liver, tones the mucous membranes of the stomach and bowel, and heals the glandular system.

Example-24

Powdered Drink Formula for Cleansing of Respiratory Tract

TABLE 21

| Ingredients | Per Serving | % DV |
|---|---|---|
| Lactoferrin* | 90 mg | † |
| Angiogenin* | 30 mg | † |
| Coenzyme Q10 | 30 mg | † |
| Vitamin-C | 60 mg | 100% |
| *Echinacea* | 1.0 g | † |
| Elder | 1.0 g | † |
| Ginger root extract | 0.5 g | † |
| Golden seal | 0.5 g | † |
| Peppermint | 0.5 g | † |

*LF and AGN can be incorporated as 120 mg (3:1) premix instead of individual ingredients.

Example-25

Powdered Drink Formula for Cleansing of the Urinary Tract

TABLE 22

| Ingredients | Per Serving | % DV |
|---|---|---|
| Lactoferrin* | 90 | † |
| Angiogenin* | 30 | † |
| Coenzyme Q10 | 30 | † |
| Vitamin-C | 60 | 100% |
| *Echinacea* root extract | 0.5 g | † |
| Golden seal root extract | 0.5 g | † |
| Grapefruit seed extract | 0.5 g | † |
| Licorice root extract | 1.0 g | † |
| Cranberry extract | 100 mg | † |
| L-theanine (decaffeinated) | 25 mg | † |

*LF and AGN can be incorporated as 120 mg (3:1) premix instead of individual ingredients.

For the above powdered drink formulae from Tables 21 and 22, may also contain pharmaceutically acceptable excipients including, but are not limited to, bicarbonate/citric acid mixtures, fructose-DC, magnesium stearate, stearic acid with flavor and color (natural or synthetic, as required). All the ingredients are blended to a homogenous mixture. This formulation may be prepared as a powder to be added to milk, water, yogurt or other food substance as a nutritional supplement.

It will be understood by those of skill in the art that numerous and various modifications can be made without departing from the spirit of the present invention.

Therefore, it should be clearly understood that the forms of the present invention are illustrative only and are not intended to limit the scope of the present invention.

What is claimed is:

1. A composition comprising isolated lactoferrin (LF) and isolated angiogenin (AGN) in a LF:AGN wt/wt ratio of from 50:1 to 9:1, wherein the concentration of LF is 10-25 wt % and wherein the concentration of AGN is 0.5-10 wt % in the composition and wherein the LF is complexed to a metal selected from the group consisting of zinc, copper, manganese, chromium, aluminum and gallium.

2. The composition of claim 1, wherein the lactoferrin is combined with an anionic compound selected from the group consisting of a carbonate, a bicarbonate, and a carbonated liquid.

3. The composition of claim 2, wherein the anionic compound is a bicarbonate.

4. The composition of claim 1, wherein the LF is complexed to copper.

5. The composition of claim 1, wherein the ratio of LF : AGN ranges between 20:1 to 9:1.

6. The composition of claim 1, further comprising an oil, a suspending agent, a flavoring agent, coloring agents or combinations thereof.

7. The composition of claim 6, wherein the oil is one or more selected from the group consisting of seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, palm oil, rapeseed oil, palm kernel oil, lupin oil, coconut oil, flaxseed oil, and evening primrose oil.

8. The composition of claim 1, further comprising a compound selected from the group consisting of phospholipids, antioxidants, vitamins, amino acids, proteins, essential minerals, lecithin and combinations thereof.

9. The composition of claim 8, wherein the composition further comprises L-carnitine, acetyl-L-carnitine or propionyl L-carnitine in an amount of 1% to 50% by weight.

10. The composition of claim 8, wherein the phospholipid is one or more selected from the group consisting of Docosahexaenoic acid (DHA), phosphatidyl glycerol, phosphatidyl inositol, phosphatidyl serine, phosphatidyl choline, phosphatidyl ethanolamine, phosphatidic acids, ceramides, cerebrosides, sphingomyelins and cardiolipins.

11. The composition of claim 8, wherein the vitamin is one or more selected from the group consisting of vitamin A, thiamine, niacinamide, pyridoxine, riboflavin, cyanocobalamin, biotin, pantothenic acid, vitamin C, vitamin D, vitamin E, vitamin K and folic acid.

12. The composition of claim 8, wherein the mineral is one or more selected from the group consisting of iron, calcium, magnesium, sodium, potassium, copper, chromium, zinc, molybdenum, iodine, boron, selenium, manganese, and combinations thereof.

13. The composition of claim 8, wherein lecithin is present in an amount of 10% to 60% by weight.

14. The composition of claim 1, further comprising a viable or a non-viable probiotic selected from the group consisting of *L. acidophilus, L. amylovorus, L. animalis, L. bavaricus, L. brevis, L. bulgaricus, L. casei* spp. *casei, L. casei* spp. *rhamnosus, L. crispatus, L. delbrueckii* ssp. *lactis, L. eichmanni, L. fermentum, L. helveticus, L. jensenii, L. kefir, L. paracasei, L. pentosus, L. plantarum, L. reuteri, L. sahvarius, L. sake, Leu. cremoris, Leu. lactis; B. adolescentis, B. animalis, B. bifidum, B. breve, B. infantis, B. longum,* and *B. thermophilum; Ped. acidilactici, Ped. pentosus, Pep. assacharolyticus, Pep. productus; Pro. acidipropionici, Pro. freudenreichii, Pro. jensenii, Pro. theonii, Strep. cremoris, Strep. faecium, Strep. lactis, Strep. raffinolactis* and *Strep. thermophilus*.

15. A formulation comprising the composition of claim 1, wherein the formulation further comprises S-adenosylmethionine.

16. A formulation comprising the composition of claim 1, wherein the formulation further comprises, at least two of the following ingredients: chondroitin sulfate, glucosamine sulfate, methylsulfonylmethane, dimethylglycine, or cerasomalcis-9-cetylmyristoleate.

17. A carbonated beverage comprising the composition of claim 1.

18. A composition according to claim 1, wherein said isolated lactoferrin and isolated angiogenin are obtained from a LF:AGN premix prepared by a method comprising:
    isolating a LF-enriched fraction from a dairy, a non-dairy or a recombinant source;
    isolating an AGN-enriched fraction from a dairy, a non-dairy or a recombinant source;
    combining the LF-enriched fraction with the AGN-enriched fraction;
    freeze-drying or spray-drying the combined fractions; and
    milling the freeze-dried or spray-dried combined fractions to obtain a LF:AGN premix.

19. The composition of claim 1, wherein the LF is complexed to zinc.

* * * * *